US007208317B2

(12) United States Patent
Threadgill et al.

(10) Patent No.: US 7,208,317 B2
(45) Date of Patent: Apr. 24, 2007

(54) IN VITRO MUTAGENESIS, PHENOTYPING, AND GENE MAPPING

(75) Inventors: David W. Threadgill, Chapel Hill, NC (US); Daekee Lee, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 235 days.

(21) Appl. No.: 10/428,977

(22) Filed: May 2, 2003

(65) Prior Publication Data
US 2004/0033596 A1  Feb. 19, 2004

Related U.S. Application Data

(60) Provisional application No. 60/377,864, filed on May 2, 2002.

(51) Int. Cl.
C12N 15/00 (2006.01)
C12N 15/01 (2006.01)
C12N 5/14 (2006.01)
C12N 5/16 (2006.01)
C12N 5/22 (2006.01)

(52) U.S. Cl. ............... 435/455; 435/468; 435/441; 435/443; 435/444; 435/446; 435/447; 435/448; 435/440; 435/325; 435/366; 435/419

(58) Field of Classification Search ............ None
See application file for complete search history.

(56) References Cited

U.S. PATENT DOCUMENTS

| | | | |
|---|---|---|---|
| 5,658,772 A | 8/1997 | Odell et al. | |
| 5,780,296 A | 7/1998 | Holloman et al. | |
| 5,789,215 A | 8/1998 | Berns et al. | |
| 5,885,836 A | 3/1999 | Wahl et al. | |
| 5,965,415 A | 10/1999 | Radman et al. | |
| 6,060,296 A | 5/2000 | Hoekstra | |
| 6,077,667 A | 6/2000 | Bradley et al. | |
| 6,139,833 A | 10/2000 | Burgess et al. | |
| 6,159,688 A | 12/2000 | Borchert et al. | |
| 6,159,690 A | 12/2000 | Borrebaeck et al. | |
| 6,207,371 B1 | 3/2001 | Zambrowicz et al. | |
| 6,232,112 B1 | 5/2001 | Catcheside | |
| 6,238,884 B1 | 5/2001 | Short et al. | |
| 6,255,113 B1 | 7/2001 | Zarling et al. | |
| 6,277,588 B1 | 8/2001 | Freeman et al. | |
| 6,277,608 B1 | 8/2001 | Hartley et al. | |
| 6,284,541 B1 | 9/2001 | Auer et al. | |
| 6,294,346 B1 | 9/2001 | Weiss et al. | |
| 6,303,327 B1 | 10/2001 | Von Melchner et al. | |
| 6,319,692 B1 | 11/2001 | Kadota et al. | |
| 6,344,356 B1 | 2/2002 | Stemmer | |
| 6,352,859 B1 | 3/2002 | delCardayre et al. | |
| 2001/0008026 A1 | 7/2001 | Schneider et al. | |
| 2002/0123058 A1 | 9/2002 | Threadgill et al. | |
| 2002/0127715 A1* | 9/2002 | Benvenisty et al. | ......... 435/366 |
| 2003/0027335 A1* | 2/2003 | Ruley et al. | ................. 435/455 |

FOREIGN PATENT DOCUMENTS

| | | |
|---|---|---|
| WO | WO99/25851 | 5/1999 |
| WO | WO99/67361 | 12/1999 |
| WO | WO00/04190 | 1/2000 |
| WO | WO00/54574 | 9/2000 |
| WO | WO01/23545 | 4/2001 |

OTHER PUBLICATIONS

Chen et al. Genotype-based screen for ENU-induced mutations in mouse embryonic stem cells. Nat Genet. vol. 24, No. 3, pp. 314-317, Mar. 2000.*
Bronstein et al. Modulation of ethylnitrosourea-induced toxicity and mutagenicity in human cells by O6-benzylguanine. Cancer Res. vol. 52, No. 14, pp. 3851-3856, Jul. 1992.*
Milstone et al. Simultaneous Cre catalyzed recombination of two alleles to restore neomycin sensitivity and facilitate homozygous mutations. Nucleic Acids Res. vol. 27, No. 15, p. e10 (pp. i/iii to iii/iii), Aug. 1999.*
Lefebvre et al. Selection for transgene homozygosity in embryonic stem cells results in extensive loss of heterozygosity. Nat Genet. vol. 27, No. 3, pp. 257-258, Mar. 2001.*
Weiss et al. In vitro differentiation of murine embryonic stem cells. New approaches to old problems. J Clin Invest. vol. 97, No. 3, pp. 591-595, Feb. 1996.*
Liu et al. Efficient Cre-loxP-induced mitotic recombination in mouse embryonic stem cells. Nat Genet. vol. 30, No. 1, pp. 66-72. Epub Dec. 10, 2001.*
Beard et al. Stress responses to DNA damaging agents in the human colon carcinoma cell line, RKO. Mutation Research, vol. 371, pp. 1-13, 1996.*
Ramirez-Solis et al. Chromosome engineering in mice. Nature, vol. 378, pges 720-724, 1995*
Zheng et al. Engineering a mouse balancer chromosome. Nature Genetics, vol. 22, pp. 375-378, 1999.*
Koike et al. Efficient biallelic mutagenesis with Cre/loxP-mediated inter-chromosomal recombination. EMBO Reports, vol. 3, No. 5, pp. 433-437, 2002.*
Adams et al., Induced mitotic recombination: a switch in time, *Nature Genetics* 30:6-7 (Jan. 2002).

(Continued)

*Primary Examiner*—Celine Qian
*Assistant Examiner*—Jennifer Dunston
(74) *Attorney, Agent, or Firm*—Jenkins, Wilson, Taylor & Hunt, P.A.

(57) ABSTRACT

Cellular libraries useful for in vitro phenotyping and gene mapping. In a representative approach, a method for preparing a homozygous cellular library includes the steps of providing a heterozygous cellular library comprising a plurality of isolated parent cells; inducing site-specific mitotic recombination in the plurality of isolated parent cells; culturing the plurality of isolated parent cells, whereby a population of daughter cells is produced; and selecting daughter cells comprising a homozygous genetic modification, whereby a homozygous cellular library is prepared.

21 Claims, 6 Drawing Sheets

OTHER PUBLICATIONS

Araki et al., Targeted integration of DNA using mutant lox sites in embryonic stem cells, *Nucleic Acids Research* 25(4):868-872 (1997).

Araki et al., Exchangeable gene trap using the Cre/mutated lox system, *Cell. Mol. Biol.* 45(5):737-750 (Jul. 1999).

Albert et al., Site-specific integration of DNA into wild-type and mutant lox sites placed in the plant genome, *Plant J.* 7(4):649-659 (Apr. 1995) (ABSTRACT).

Abbate et al., Bifunctional protein conferring enhanced green fluorescence and puromycin resistance, *Biotechniques* 31(2):336-340 (Aug. 2001) (ABSTRACT).

Beckers et al., Large-scale mutational analysis for the annotation of the mouse genome, *Proteomics and Genomics* 17-23 (published online Nov. 29, 2001).

Bentley et al., DNA ligase I null mouse cells show normal DNA repair activity but altered DNA replication and reduced genome stability, *J. Cell Sci.* 115(7):1551-1561, (Apr. 2002).

Blake, et al., The Mouse Genome Database (MGD): the model organism database for the laboratory mouse, *Nucleic Acids Research* 30(1):113-115 (2002).

Buchholz et al., Improved properties of FLP recombinase evolved by cycling mutagenesis, *Nat Biotechnol.* 16)7):657-662 (Jul. 1998) (ABSTRACT).

Chen et al., CREating breakthroughs, *Nature Biotechnology* 19:921-922 (Oct. 2001).

Chen, et al., A new positive/negative selectable marker, puDeltatk, for use in embryonic stem cells, *Genesis* 28(1):31-35 (Sep. 2000) (ABSTRACT).

Cohen-Tannoudji et al., I-SceI-Induced Gene Replacement at a Natural Locus in Embryonic Stem Cells, *Molecular and Cellular Biology* 18(3):1444-1448 (Mar. 1998).

Derossi et al., Trojan peptides: the penetratin system for intracellular delivery, *Cell Biology* 8:84-87 (Feb. 1998).

De Berardino, Animal Cloning—the route to new genomics in agriculture and medicine, *Differentiation* 68:67-83 (2001).

Duffy et al., Identifying loci required for follicular patterning using directed mosiacs, *Development* 125:2263-2271 (1998).

Esposito et al., The integrase family of tyrosine recombinases: evolution of a conserved active site domain, *Nucleic Acids Research* 25(18):3605-3614 (1997).

Farley et al., Widespread Recombinase Expression Using FLPeR (Flipper) Mice, *Genesis* 28:106-110 (2000).

Flaherty, Generation, Identification, and Recovery of Mouse Mutations, *METHODS: A Companion to Methods in Enzymology* 14:107-118 (1998).

Grainge et al., *The integrase family of recombinase: organization and function of the active site, Mol Microbiol.* 33(3):449-456 (Aug. 1999) (ABSTRACT).

Groth et al., A phage integrase directs efficient site-specific integration in human cells, *PNAS* 97(11):5995-6000 (May 23, 2000).

Halbert et al., Adeno-associated Virus Vectors Transduce Primary Cells Much Less Efficiently then Immortalized Cells, *J. of Virology* 69(3):1473-1479 (Mar. 1995).

Hanin et al., Gene targeting in Arabidopsis, *The Plant Journal* 28(6):671-677 (2001).

Hérault et al., Engineering chromosomes in mice through targeted meiotic recombination (TAMERE), *Nature Genetics* 20:381-384 (Dec. 1998).

Hrabé de Angelis et al., Genome-wide large-scale production of mutant mice by ENU mutagenesis, *Nature Genetics* 25:444-447 (Aug. 2000).

Isaacs et al., Identification of two new pmp22 mouse mutants using large-scale mutagenesis and a novel rapid mapping strategy, *Human Molecular Genetics* 9(12):1865-1871 (2000).

Jo et al., Epigenetic regulation of gene structure and function with a cell-permeable Cre recombinase, *Nature Biotechnology* 19:929-933 (Oct. 2001).

Kanbashi et al., Frameshifts, base substitutions and minute deletions constitute X-ray-induced mutations in the endogenous tonB gene of *Escherichia coli* K12, *Mutation Research* 385:259-267 (1997).

Kanegae et al., Efficient gene activiation in mammalian cells by using recombinant adenovirus expressing site-specific Cre recombinase, *Nucleic Acids Research* 23(19):3816-3821 (Oct. 1995) (ABSTRACT).

Kolot et al., Site-specific recombination in mammalian cells expression the Int recombinase of bacteriophage HK022, *Mol. Biol. Rep.* 26(3):207-213 (Aug. 1999)(ABSTRACT).

Kurtzman et al., Advances in directed protein evolution by recursive genetic recombination: applications to therapeutic proteins, *Biotechnology* 12:361-370 (2001).

Lebel et al., A deletion within the murine Werner syndrome helicase induces sensitivity to inhibitors of topoisomerase and lose of cellular proliferative capacity, *Proc. Natl. Acad. Sci. USA* 95:13097-13102 (Oct. 1998).

Lee et al., Role of nucleotide sequences of loxP spacer region in Cre-mediated recombination, *Gene* 216:55-65 (1998).

Lindgren et al., Cell-penetrating peptides, *TiPS* 21:99-103 (Mar. 2000).

Maeser et al. The Gin recombinase of phage Mu can catalyse site-specific recombination in plant protoplasts, *Mol Gen Genet* 230(1-2):170-176 (Nov. 1991) (ABSTRACT).

Moore et al., Cell-based versus isolated target screening: how lucky to you feel?, *J. Biomol Screen* 6(2):69-74 (Apr. 2001)(ABSTRACT).

Myers et al., X and the RecBCD enzyme of *Escherichia coli*, *Annual Review of Genetics*, Annual 28:49 (1994).

Nagy, Cre Recombinase: The Universal Reagent for Genome Tailoring, *Genesis* 26:99-109 (2000).

Nolan et al., A systematic, genome-wide, phenotype-driven mutagenesis programme for gene function studies in the mouse, *Nature Genetics* 25:440-443 (Aug. 2000).

Odorico et al., Multilineage Differentiation from Human Embryonic Stem Cell Lines, *Stem Cells* 19:193-204 (2001).

Oh et al., Generation of fusion genes carrying drug resistance, green fluorescent protein, and herpes simplex virus thymidine kinase genes in a single cistron, *Mol Cells* 11(2):192-197 (Apr. 30, 2001) (ABSTRACT).

Olivares et al., Phage R4 integrase mediates site-specific integration in human cells, *Gene* 278:167-176 (2001).

Oram et al., Recombination. Pieces of the site-specific recombination puzzle, *Curr Biol* 5(10):1106-1109 (Oct. 1, 1995) (ABSTRACT).

Pekrun et al., Evoluation of human immunodeficiency virus type1 variant with enhanced replication in pig-tailed macaque cells by DNA shuffling, *J. Virol.* 76(6):2924-2935 (Mar. 2002) (ABSTRACT).

Prochiantz, Messenger proteins: homeoproteins, TAT and others, *Cell Biology* 12:400-406 (2000).

Ravatn et al., Int-B13, an unusual site-specific recombinase of the bacteriophage P4 integrase family, is responsible for chromosomal insertion of the 105-kilobase clc element of Pseudomonas sp. Strain B13, *J. Bacteriol.* 180(21):5505-5514 (Nov. 1998) (ABSTRACT).

Rinaldi, et al., A non-cytotoxic herpes simplex virus vector which expresses Cre recombinase directs efficient site specific recombination, *Virus Res.* 65(1):11-20 (Dec. 1, 1999) (ABSTRACT).

Rossant et al., Mouse-based phenogenomics for modeling human disease, *TRENDS in Molecular Medicine* 7(11):502-507 (Nov. 2001).

Schlake et al., Use of mutated FLP recognition target (FRT) sites for the exchange of expression cassettes at defined chromosomal loci, *Biochemistry* 33(43):12746-12751 (Nov. 1, 1994)(ABSTRACT).

Schwarze et al., In vivo protein transduction: intracellular delivery of biologically active proteins, compounds and DNA, *TiPS* 21:45-48 (Feb. 2000).

Sclimenti et al., Directed evolution of a recombinase for improved genomic integration at a native human sequence, *Nucleic Acids Res.* 29(24):5044-5051 (Dec. 15, 2001) (ABSTRACT).

Sedivy et al., Gene Targeting in Human Cells Without Isogenic DNA, *Science* 283:9a (Jan. 1, 1999).

Serre et al., Cleavage properties of an archaeal site-specific recombinase, the SSV1 integrase, *J. Biol. Chem* epub ahead of print (Mar. 1, 2002) (ABSTRACT).

Snaith et al., Multiple cloning sites carrying loxP and FRT recognition sites for the Cre and Flp site-specific recombinases, *Gene* 166:173-174 (1995).

Stark, et al., Site-specific recombination of Tn2 resolvase, *Trends Genet* 5(9):304-309 (Sep. 1989) (ABSTRACT).

Sundberg, High-throughput and ultra-high-throughput screening: solution- and cell-based approaches, *Biotechnology* 11:47-53 (2000).

Tanaka et al., A highly efficient method for the site-specific integration of transfected plasmids into the genome of mammalian cells using purified retroviral integrase, *Gene* 216(1):67-76 (Aug. 17, 1998) (ABSTRACT).

Thyagarajan et al., Site-specific genomic integration in mammalian cells mediated by phage phiC31 integrase, *Mol Cell Biol* 21(12):3926-3934 (Jun. 2001) (ABSTRACT).

Tirumalai et al., The catalytic domain of lambda site-specific recombinase, *Proc Natl Acad Sci USA* 94(12):6104-6109 (Jun. 10, 1997) (ABSTRACT).

Woychik et al., Functional genomics in the post-genome era, *Mutation Research* 400:3-14 (1998).

Wu et al., Substrate-specific inhibition of RecQ helicase, *Nucleic Acids Research* 29(8):1765-1771 (2001).

Xu et al., Analysis of genetic mosaics in developing and adult Drosophila tissues, *Development* 117:1223-1237 (1993).

Yaspo, Taking a functional genomics approach in molecular medicine, *TRENDS in Molecular Medicine* 7(11):494-502 (Nov. 2001).

Yu et al., Engineering Chromosomal Rearrangements in Mice, *Nature* 2:780-790 (Oct. 2001).

Zambrowicz et al., Disruption and sequence identification of 2,000 genes in mouse embryonic stem cells, *Nature* 392(6676):608-611 (Apr. 9, 1998) (ABSTRACT).

Zhang et al., Towards genetic genome projects: genomic library screening and gene-targeting vector construction in a single step, *Nat. Genet* 30(1):31-39 (Jan. 2002).

Zhang et al., Genome shuffling leads to rapid phenotypic improvement in bacteria, *Nature* 415:644-646 (Feb. 7, 2002).

Zheng et al., Engineering Mouse Chromosomes with Cre-loxP: Range, Efficiency, and Somatic Applications, *Molecular and Cellular Biology* 20(2):648-655 (Jan. 2000).

Burns et al., Large-scale analysis of gene expression, protein localization, and gene disruption in *Saccharomyces cerevisiae*, *Genes & Development* 8:1087-1105 (1994).

Kurtz and Marrinan, Isolation of Hem3 mutants from *Candida albicans* by sequential gene disruption, *Mol. Gen. Genet.* 217:47-52 (1989).

International Preliminary Examination Report corresponding to the International Patent Application Serial No. PCT/US03/13625 dated Aug. 8, 2006.

\* cited by examiner

IN VITRO MUTAGENESIS, PHENOTYPING, AND GENE MAPPING

CROSS REFERENCE TO RELATED APPLICATIONS

This application is based on and claims priority to U.S. Provisional Application Ser. No. 60/377,864, filed May 2, 2002, herein incorporated by reference in its entirety.

GRANT STATEMENT

This work was supported by grant CA79869 from the U.S. National Institutes of Health (NIH). Thus, the U.S. government has certain rights in the presently disclosed subject matter.

TECHNICAL FIELD

The presently claimed subject matter pertains to novel cellular libraries useful for phenotypic screening and gene mapping.

| Table of Abbreviations | |
| --- | --- |
| 6-MP - | 6-mercaptopurine |
| 6-TG - | 6-thioguanine |
| 6-TX - | 6-thioxanthine |
| AA - | acrylamide monomer |
| att - | Int recombination site |
| attB - | Int recombination site |
| attP - | Int recombination site |
| β-geo - | β-galactosidase/neomycin fusion |
| CAD - | carbamoyl-phosphate synthetase 2/ aspartate transcarbamylase/ dihydroorotase |
| CaMV - | Cauliflower Mosaic Virus |
| CFP - | cyan fluorescent protein |
| CHL - | chlorambucil |
| cM - | centimorgan |
| CPP - | cyclophosphamide |
| CT - | computerized tomography |
| DES - | diethyl sulfate |
| DMSO - | dimethylsulfoxide |
| EC - | embryonic carcinoma (cell) |
| EDTA - | ethylene diamine tetraacetic acid |
| EG - | embryonic germ (cell) |
| EMS - | ethyl methane sulfonate |
| ENU - | N-ethyl-N-nitrosurea |
| ES - | embryonic stem (cell) |
| ESI-MS - | electrospray ionization mass spectrometry |
| FACS - | fluorescence-activated cell sorter |
| FIAU - | 2'-fluoro-2'-deoxy-1-β-D-arabinofuranosyl-5-iodo-uracil |
| FLP - | FLP recombinase |
| FLPe - | enhanced FLP recombinase |
| FRT - | FLP recombination site |
| GC-MS - | gas chromatography-mass spectrometry |
| GFP - | green fluorescent protein |
| HAT - | hypoxanthine-aminopterin-thymidine |
| HBSS - | Hank's Balanced Salt Solution |
| His$_6$ - | peptide of 6 histidine residues |
| His$_6$-NLS-Cre-MTS - | cell-permeable Cre recombinases |
| HPLC - | high performance liquid chromatography |
| HPRT - | hypoxanthine guanine phosphoribosyltransferase |
| HSVtk - | herpes simplex virus thymidine kinase |
| IHF - | integration host factor |
| Int - | integrase recombinases |
| kb - | kilobase(s) |
| LC-MS - | liquid chromatography-mass spectrometry |
| LDLR - | low-density lipoprotein receptor |
| LD-MS - | laser-desorption mass spectrometry |
| LIF - | leukemia inhibitory factor |
| LNGFR - | low-affinity nerve growth factor receptor |
| LOD - | logarithmic odds ratio |
| Lox - | Cre recombination site |
| LoxP - | wild type lox site |
| Lox66 - | mutant lox site |
| Lox71 - | mutant lox site |
| LRS - | likelihood ratio statistic |
| M - | Morgan |
| MALDI-MS - | matrix-assisted laser desorption/ ionization mass spectrometry |
| MALDI-TOF - | matrix-assisted laser desorption/ ionization - time-of-flight |
| MCI - | a synthetic herpes simplex virus thymidine kinase promoter |
| MLP - | melphalan |
| MMC - | mitomycin C |
| MMS - | methyl methane sulfonate |
| MNNG - | N-methyl-N'-nitro-N-nitrosoguanidine |
| MNU - | methylnitrosourea |
| MRI - | magnetic resonance imaging |
| MTS - | membrane translocating sequence |
| MTT - | 3-(4,5-dimethylthiazole-2-yl)-2,5-diphenyl tetrazolium bromide |
| NLS - | nuclear localization signal |
| NEO - | neomycin |
| NMM - | N-methyl mesoporphyrin IX |
| NSM - | negative selectable marker |
| PCR - | polymerase chain reaction |
| PGK - | phosphoglycerate kinase I |
| PMEF - | primary mouse embryonic fibroblast |
| PRC - | procarbazine |
| PSM - | positive selectable marker |
| PURO - | puromycin |
| Puro$^r$ - | puromycin resistance |
| RecQ - | a helicase |
| RFLP - | restriction fragment length polymorphism |
| RIST - | Recombinant Inbred Segregation Test |
| RLGS - | restriction landmark genomic scanning |
| RS - | recombination site |
| SNP - | single nucleotide polymorphism |
| SSLP - | short sequence length polymorphism |
| STRP - | short tandem repeat polymorphism |
| TEM - | triethylene melamine |
| tk - | thymidine kinase |
| TOF-MS - | time-of-flight mass spectrometry |
| UR - | urethane |
| UV - | ultraviolet |
| XTT - | 2,3-Bis(2-methoxy-4-nitro-5-sulfophenyl)-2H-tetrazolium-5-carboxanilide |
| YFP - | yellow fluorescent protein |

BACKGROUND ART

Complete or draft versions of genome sequences have been obtained in a variety of organisms, including human (Hattori et al., 2000; Lander et al., 2001; McPherson et al., 2001; Sachidanandam et al., 2001; Venter et al., 2001), and a large fraction of the genes are also mapped to chromosomal regions. A current challenge is to annotate gene maps with phenotypic information that imparts functional meaning to the genomic sequences. Thus, genomic research efforts have shifted to systematic determination of gene function (e.g., via analysis of mutant phenotypes). See e.g., Parinov & Sundaresan, 2000; Beckers & Angelis, 2001; Rossant & McKerlie, 2001; Yaspo, 2001. The ability to link a phenotype with one or more genes responsible for that trait provides opportunities for new diagnostics and treatments of genetic diseases.

Large-scale random mutagenesis approaches have generally relied on creating or inducing genetic modifications, the impact of which are evaluated in the context of a complete organism. Screening approaches for the selection of both dominant and recessive mutations are available in plant and animal model organisms, including *Drosophila melanogaster* (Gans et al., 1975; Nusslein-Volhard & Wieschaus, 1980), *Caenorhabditis elegans* (Brenner, 1974; Kemphues et al., 1988), *Arabidopsis thaliana* (Budziszewski et al., 2001; McElver et al., 2001), *Danio rerio* (Driever et al., 1996; Haffter et al., 1996), and *Mus musculus* (see citations below). For recovery of mutations that confer early organismal lethality, methods have been developed for the systematic generation of mosaic animals bearing homozygous mutant clones. See e.g., Xu et al., 1995; Duffy et al., 1998.

For insights into human disease, the mouse is an experimental genetic system of choice because its genes, biochemical pathways, and physiological organ functions are closely related to those in humans. Random mutagenesis screens in mouse initially focused on screens for dominant mutations that result in viable, clinically relevant phenotypes (Hrabe de Angelis et al., 2000; Isaacs et al., 2000; Nolan et al., 2000). Genome-wide screens that select recessive mutations (Kasarskis et al., 1998; Fahrer et al., 2001) and screens based on mosaic analysis (Liu et al., 2002) have more recently been undertaken.

Since phenotypic screens have relied on whole organism analysis, systematic mutagenesis studies have been limited to model genetic organisms. Thus, a functional genomics approach has generally not been available in most organisms, including humans, agriculturally important plants and animals, domestic animals, pathogens, etc. However, genomic sequencing has been accomplished or is currently sought in many non-model organisms, and functional annotation is similarly valuable.

A reverse genetics strategy called double-stranded RNA interference has been developed recently as a method for functional analysis in non-model organisms. According to this approach, double-stranded RNA is used to target specific RNA transcripts for degradation, thereby leading to a loss of gene function. Since the double-stranded RNA is prepared based on known sequence, the link between gene and phenotype is already known.

RNA interference is a silencing phenomenon that is manifest in plants, animals and fungi, and therefore enables systematic functional analysis of any organism for which genomic sequence data is known. See Zamore, 2001; Carthew, 2001. This strategy has been adopted for genome-wide analysis in C. elegans (Bargmann, 2001). Despite its utility in diverse organisms, RNA interference is limited to loss-of-function analysis. Thus, this strategy is inapplicable for the discovery of disease-related mutations resulting from increased or otherwise altered gene function.

Thus, current and long-felt needs in the field include strategies for rapid phenotyping and gene mapping that can be performed in any species. The presently claimed subject matter discloses methods for generating, phenotyping, and mapping mutations in vitro, and thus addresses the current and long-felt need in the art for the same.

SUMMARY

The presently claimed subject matter provides cellular libraries useful for in vitro phenotyping and gene mapping, and methods for using the same.

In one embodiment of the presently claimed subject matter, a heterozygous cellular library is provided, the heterozygous cellular library comprising a randomly mutagenized population of isolated cells, wherein each of the isolated cells comprises a marked chromosome comprising a dominant positive selectable marker.

Each cell of a randomly mutagenized population of isolated cells can comprise one or more heterozygous genetic modifications. In one embodiment, the one or more heterozygous genetic modifications are produced by a method selected from the group consisting of chemical mutagenesis, ultraviolet radiation, X-ray radiation, exposure to inhibitors of DNA repair, and combinations thereof.

The presently claimed subject matter also provides methods for preparing a heterozygous cellular library. A representative embodiment of the method comprises: (a) providing a plurality of isolated cells, wherein each of the plurality of isolated cells comprises a dominant positive selectable marker; and (b) randomly mutagenizing the plurality of isolated cells, whereby a heterozygous cellular library is prepared.

In another embodiment of the presently claimed subject matter, a homozygous cellular library is provided, the homozygous cellular library comprising a randomly mutagenized and homozygosed population of isolated cells. In one embodiment, each cell of a randomly mutagenized and homozygosed population of isolated cells comprises one or more homozygous genetic modifications.

The presently claimed subject matter also provides methods for preparing a homozygous cellular library. A representative embodiment of the method comprises: (a) providing a heterozygous cellular library comprising a plurality of isolated parent cells; (b) inducing site-specific mitotic recombination in the plurality of isolated parent cells; (c) culturing the plurality of isolated parent cells, whereby a population of daughter cells is produced; and (d) selecting daughter cells comprising a homozygous genetic modification, whereby a homozygous cellular library is prepared.

In accordance with the disclosed methods for preparing a homozygous cellular library, each of the plurality of isolated parent cells can further comprise a marked chromosome pair, wherein the marked chromosome pair comprises a first chromosome and a second homologous chromosome, wherein the first chromosome comprises a first recombination cassette, and wherein the second homologous chromosome comprises a second allelic recombination cassette. In one embodiment, the first and second recombination cassettes each comprise a centromeric position.

A recombination cassette comprises a recombination site, for example, a lox site, an FRT site, or an att site. In one embodiment, a first recombination cassette and a second recombination cassette can recombine to produce a stable first recombination event. For example, in an exemplary embodiment of the presently claimed subject matter, a first recombination cassette comprises a lox66 site, and a second recombination cassette comprises a lox71 site. In another embodiment of the presently claimed subject matter, a first recombination cassette comprises an attB site, and a second recombination cassette comprises an attP site.

A recombination cassette can further comprise one or more selectable markers to facilitate in vitro phenotyping and gene mapping. For example, a first recombination cassette of a marked chromosome pair can comprise a first selectable marker, and a second recombination cassette of the marked chromosome pair can comprise a second selectable marker. In one embodiment, a selectable marker comprises a dominant negative selectable marker or a recessive positive selectable marker.

A site-specific recombinase used to induce mitotic recombination via the recombination cassettes can comprises a site-specific recombinase selected from the group consisting of a Cre recombinase, a FLP recombinase, and an Int recombinase. A site-specific recombinase comprises in one embodiment a cell-permeable recombinase and in another embodiment a cell-permeable Cre recombinase.

Cells of a cellular library can be isolated from any organism, including both plants and animals. In one embodiment of the presently claimed subject matter, a library of the presently claimed subject matter comprises human cells.

Cells of a cellular library can comprise any suitable cell type, including stem cells, precursor cells, and differentiated cells. In one embodiment of the presently claimed subject matter, a cellular library comprises embryonic stem (ES) cells.

Stem cells and precursor cells of a cellular library can be induced to differentiate in vitro. For example, differentiation can be induced prior to mutagenesis, following mutagenesis and prior to phenotyping, or as part of a phenotyping assay.

In one embodiment, the heterozygous cellular libraries and homozygous cellular libraries of the presently claimed subject matter each comprise a population of genetically related cells.

The presently claimed subject matter further provides a kit for in vitro phenotyping and gene mapping. A kit of the presently claimed subject matter comprises: (a) a heterozygous cellular library comprising a randomly mutagenized population of isolated parent cells; and (b) a homozygous cellular library comprising a randomly mutagenized and homozygosed population of isolated daughter cells, wherein the homozygous library is derived from the heterozygous cellular library. In one embodiment, each parent cell of the heterozygous cellular library comprises a unique identifier, and each daughter cell produced by homozygosing a parent cell comprises a same unique identifier.

The cellular libraries of the presently claimed subject matter are useful for in vitro phenotyping and gene mapping, as disclosed herein. A phenotype can comprise any observable trait, including but not limited to a visible phenotype, a viability phenotype, a molecular phenotype, a differentiation phenotype, a cell behavioral phenotype, a susceptibility phenotype, a resistance phenotype, and combinations thereof. A genetic locus conferring a phenotype of interest can then be mapped using the disclosed methods.

In a representative embodiment of the presently claimed subject matter, a method for in vitro phenotyping comprises: (a) providing a heterozygous cellular library or a homozygous cellular library; (b) assaying the cellular library for a phenotype of interest; and (c) selecting one or more cells that displays the phenotype of interest.

Representative gene mapping methods provided by the presently claimed subject matter comprise: (a) culturing an isolated cell comprising one or more heterozygous genetic modifications, whereby a population of recombinant cells is produced; and (b) mapping the genomes of individuals within the population of recombinant cells that display a phenotype, whereby a genetic locus that modulates the phenotype is identified. The mapping can comprise, for example, analyzing genetic polymorphisms segregating in the population of recombinant cells.

In accordance with the mapping methods of the presently claimed subject matter, the culturing step can further comprise contacting the culture with an inhibitor of DNA repair to thereby promote mitotic recombination. A representative inhibitor of DNA repair comprises a helicase inhibitor, in one embodiment a RecQ helicase inhibitor. Inhibitor compounds that can be used in accordance with the disclosed methods include, but are not limited to porphyrin and porphyrin derivatives, for example meso-tetra(N-methyl-4-pyridyl)porphine tetra tosylate (T4) or N-methyl mesoporphyrin IX (NMM).

The presently claimed subject matter further provides a method for in vitro phenotyping and gene mapping comprising: (a) phenotyping a cellular library; (b) selecting a cell comprising a genetic modification that confers a phenotype of interest; (c) culturing a cell that is heterozygous for the genetic modification, whereby a population of recombinant cells is produced; and (d) mapping the genomes of individuals within the population of recombinant cells, whereby a genetic locus that modulates the phenotype is identified. The disclosed method for in vitro phenotyping and gene mapping can employ a heterozygous cellular library or a homozygous cellular library.

Thus, an object of the presently claimed subject matter is to provide novel cellular libraries, and phenotyping and gene mapping methods employing the same. This object has been met in whole or in part by the presently claimed subject matter.

An object of the presently claimed subject matter having been stated hereinabove, other objects will become evident as the description proceeds when taken in connection with the accompanying Drawings and Examples as best described herein below.

BRIEF DESCRIPTION OF THE DRAWINGS

FIG. 5A is a schematic drawing depicting preparation of a homozygous cellular library using the heterozygous cellular library of FIG. 4.

FIG. 5B is a schematic drawing depicting chromosomal events as cells of the heterozygous library of FIG. 4 are expanded in the presence of Cre, 6-TG, puromycin, and neomycin, to thereby produce a homozygous cellular library. Following Cre-induced mitotic recombination, cells comprising a homozygous mutation (circled) are selected based on resistance to puromycin, neomycin, and 6-TG. Puro, puromycin; Neo, neomycin; 6-TG, 6-thioguanine; R, resistant; S, susceptible; ⨉, random mutation.

DETAILED DESCRIPTION

I. Definitions

While the following terms are believed to be well understood by one of ordinary skill in the art, the following definitions are set forth to facilitate explanation of the presently claimed subject matter.

Following long-standing patent law convention, the terms "a" and "an" mean "one or more" when used in this application, including the claims.

The terms "nucleic acid molecule" and "nucleic acid" each refer to deoxyribonucleotides or ribonucleotides and polymers thereof in single-stranded, double-stranded, or triplexed form. Unless specifically limited, the term encompasses nucleic acids containing known analogues of natural nucleotides that have similar properties as the reference natural nucleic acid. The terms "nucleic acid molecule" and "nucleic acid" can also be used in place of "gene", "cDNA", or "mRNA."

The term "gene" refers broadly to any segment of DNA associated with a biological function. A gene encompasses sequences including, but not limited to a coding sequence, a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof.

The term "locus" refers to a chromosomal location of a gene.

The term "genotype" refers to the genetic constitution of a cell or organism, e.g. genomic nucleic acid material.

The term "phenotype" generally refers to any observable character of a cell or organism, as described further herein below.

The term "cell" refers to a single cell or a plurality of clonal cells. Thus, the term "cell" encompasses a population of cells produced by clonal expansion of a single cell.

The terms "first" and "second", for example, as used herein to describe homologous chromosomes, recombination cassettes, markers, etc., are included for clarity of description and are not meant to be limiting.

The term "about", as used herein when referring to a measurable value such as a position of a locus (e.g., in cM), target gene strength, power, etc., is meant to encompass variations of in one embodiment ±20% or ±10%, in another embodiment ±5%, in another embodiment ±1%, and in still another embodiment ±0.1% from the specified value, as such variations are appropriate to perform the disclosed method.

II. Cellular Libraries

Figure 1:
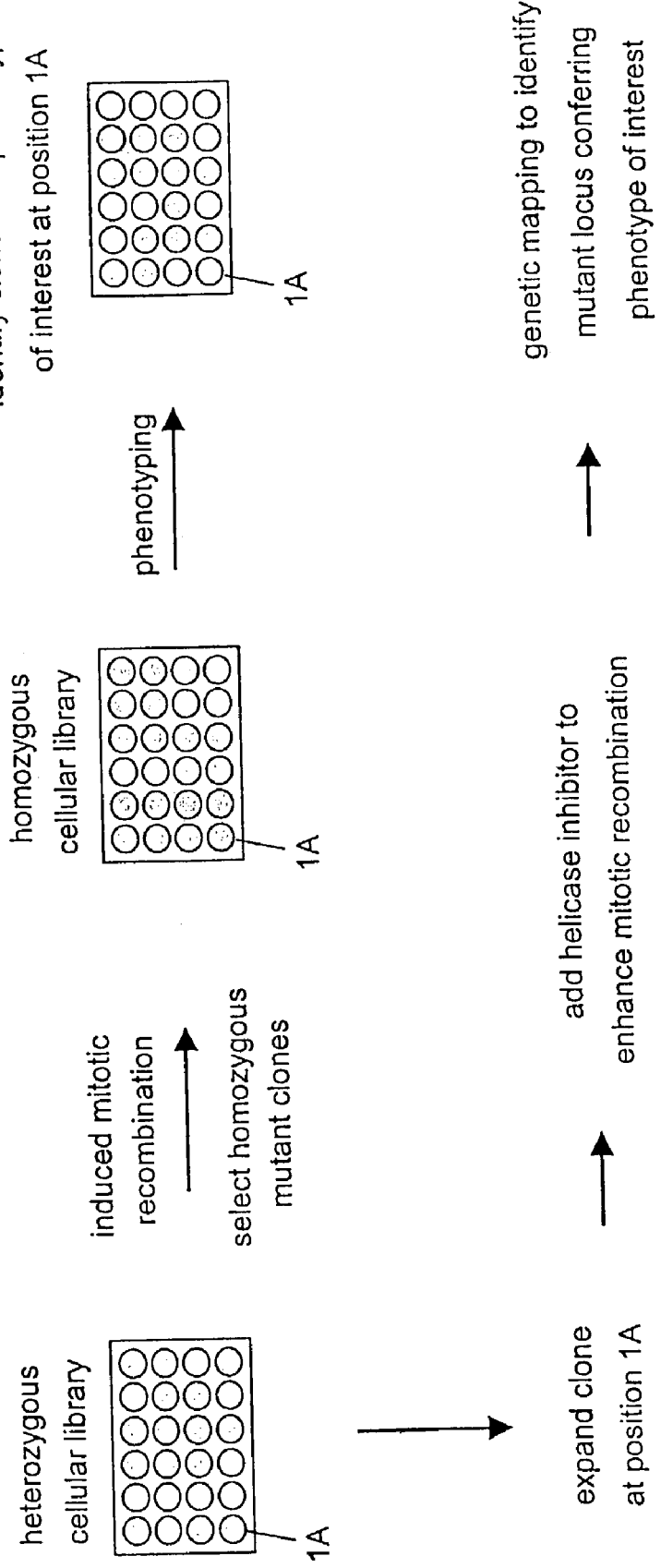
FIG. 1 depicts a summary of the disclosed methods for in vitro phenotyping and gene mapping.

The presently claimed subject matter provides cellular libraries and methods for preparing the same. In accordance with the methods disclosed herein, the cellular libraries can be used for in vitro phenotyping and gene mapping, as described herein below. See FIG. 1.

The term "cellular library" is used herein to describe a plurality of isolated cells comprising diverse genetic material, wherein each of the plurality of cells comprises one or more random genetic modifications relative to other cells within the cellular library. Each cell of a cellular library is referred to as a "genetic variant."

The term "genetic variant" is used herein to describe genomic nucleic acid material comprising one or more genetic modifications, or to a cell comprising the same. Thus, in one embodiment, each of a plurality of cells of a cellular library prepared as disclosed herein comprises a "genetic variant". A genetic variant can comprise a homozygous or heterozygous genetic modification.

In one embodiment, a cellular library of the presently claimed subject matter comprises a population of genetically related cells. The term "genetically related", as used herein to compare two or more cells, refers to a common cellular origin. Thus, the genomic nucleic acid material of two or more genetically related cells is substantially identical.

The term "substantially identical" refers to genetic identity other than variation produced by: (a) spontaneous mutation; (b) random mutagenesis among genetically identical members of a population; or (c) a combination thereof. Thus, a mutagenized population of initially identical cells are "genetically related. In contrast, the term "genetically related", as used herein to describe a population of cells, excludes a collection of mutants from diverse sources, for example a collection of naturally occurring mutants or a collection of individually targeted mutations.

The term "isolated", as used herein to describe a population of cells, refers to a quality of being separate from an organism. For example, the term "isolated cell" refers to a cell that is isolated away from an organism and can be maintained in culture.

The term "culture", as used herein to describe a cell culture, refers to any in vitro setting for cell growth. The term "culture" encompasses the culture of immortal cell lines, primary cell cultures, non-transformed cell lines, and any other cell population that can be maintained in vitro.

In one embodiment, a cellular library of the presently claimed subject matter comprises about 100 members to about 5000 members, or more. A cellular library comprising members having multiple marked chromosome pairs can comprise about 100 members to about 100,000 members, or more. The number of members in a library can be optimized to achieve saturation mutagenesis, wherein a mutant form of each gene is represented.

In another embodiment, each cell of a cellular library comprises a unique identifier. In one embodiment of the presently claimed subject matter, a cellular library is spatially arrayed, such that each cell of the cellular library can be identified according to its unique position within the array. For example, a cellular library can be maintained in multi-well plates, and a unique location identity of each cell can be expressed as a plate number and well number.

Cellular libraries of the presently claimed subject matter can be replicated as desired for various applications, including preparing a homozygous cellular library, phenotyping a cellular library, and mapping a genetic locus that confers a phenotype of interest, as described herein below. The term "replicate" refers to the accurate duplication of an original cellular library of the presently claimed subject matter to produce a replica cellular library. Thus, the unique identifier of each cell is identical, or otherwise traceable, in the original and replica libraries.

To facilitate arraying and replicating cellular libraries, automated cell-culturing equipment can be employed, such as the MULTIMEK™96 multi-well pipetter and the BIOMEK®2000 liquid handling workstation (both available from Beckman Instruments, Inc., Fullerton, Calif., United States of America).

In accordance with the methods of the presently claimed subject matter, cellular libraries can be provided in the form of a kit useful for performing in vitro phenotyping and gene mapping as disclosed herein. For example, a kit can comprise a heterozygous cellular library, a homozygous cellular library, or a combination thereof.

The presently claimed subject matter further provides that cellular libraries can be frozen and transported while frozen to remote locations for performance of in vitro phenotyping and/or gene mapping. Representative methods for cryopreservation of cellular libraries are described in Example 3. Additional methods for preparation and handling of frozen cells can be found in Freshney, 1987 and U.S. Pat. Nos. 6,176,089; 6,140,123; 5,629,145; and 4,455,842; among other places.

Heterozyqous Cellular Libraries. The term "heterozygous cellular library" refers to a library comprising a randomly mutagenized population of isolated cells. A cell of a heterozygous cellular library comprises a random genetic variant.

The term "random genetic variant" refers to a genetic modification induced via random mutagenesis. Random genetic modifications are typically heterozygous, and hence the term "heterozygous cellular library".

In one embodiment, each of the cells of a heterozygous cellular library comprises a marked chromosome comprising a dominant positive selectable marker. The term "marked chromosome" refers to a chromosome comprising a selectable marker that enables identification of cells comprising the marked chromosome in a population of cells, including similar cells that lack the selectable marker. Selection of marker nucleic acids and preparation of marked chromosomes are described further herein below.

PCT International Publication No. WO 99/67361 to Woychik et al. discloses a heterozygous cellular library. In contrast to Woychik et al., the presently claimed subject matter provides that cells of a heterozygous cellular library can comprise one or more marked chromosomes to facilitate in vitro phenotyping and gene mapping, among other distinctions. The marked chromosomes also facilitate preparation of a homozygous cellular library, which is not readily accomplished in the absence of a marked chromosome.

Figure 2:
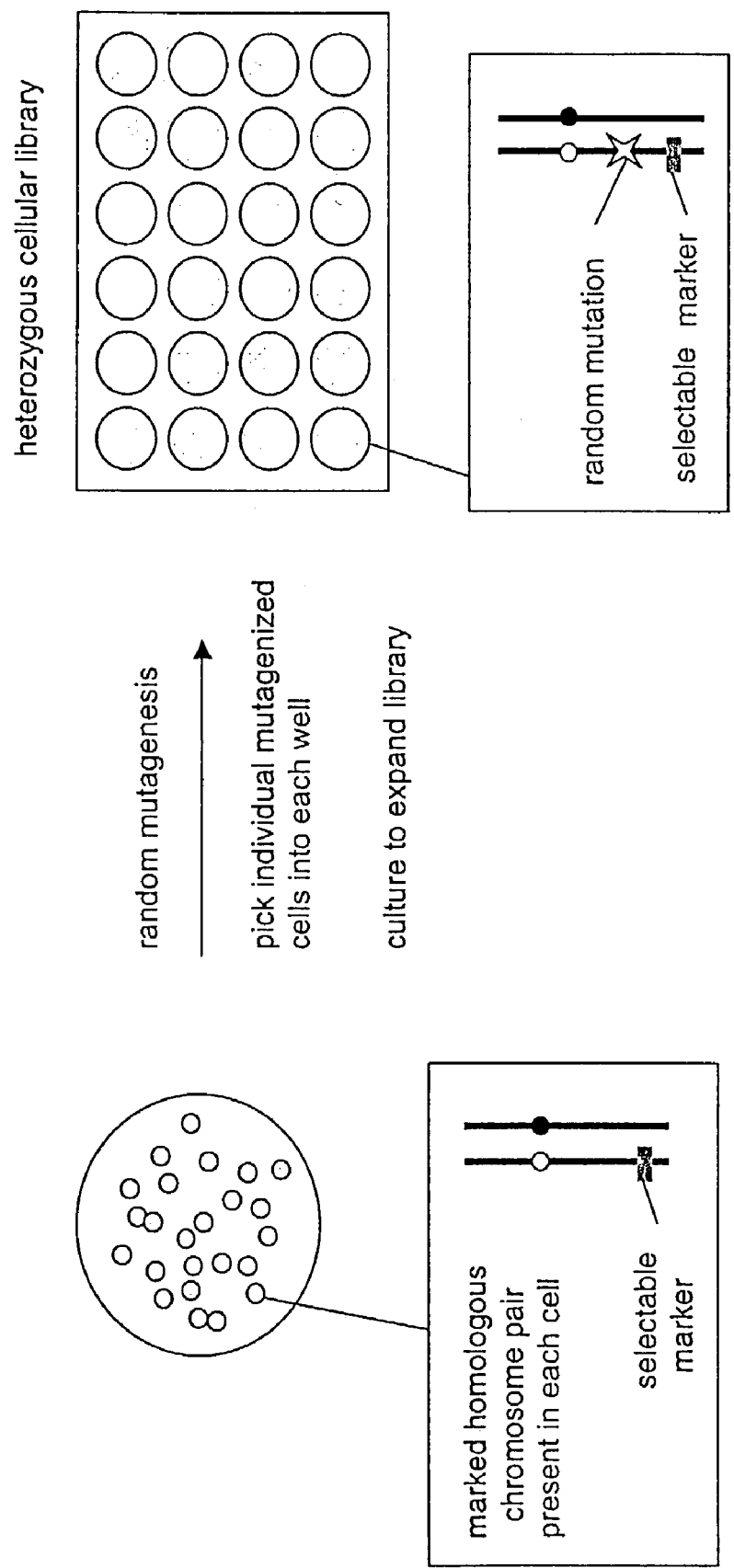
FIG. 2 is a schematic drawing depicting preparation of a heterozygous cellular library.
Figure 4:
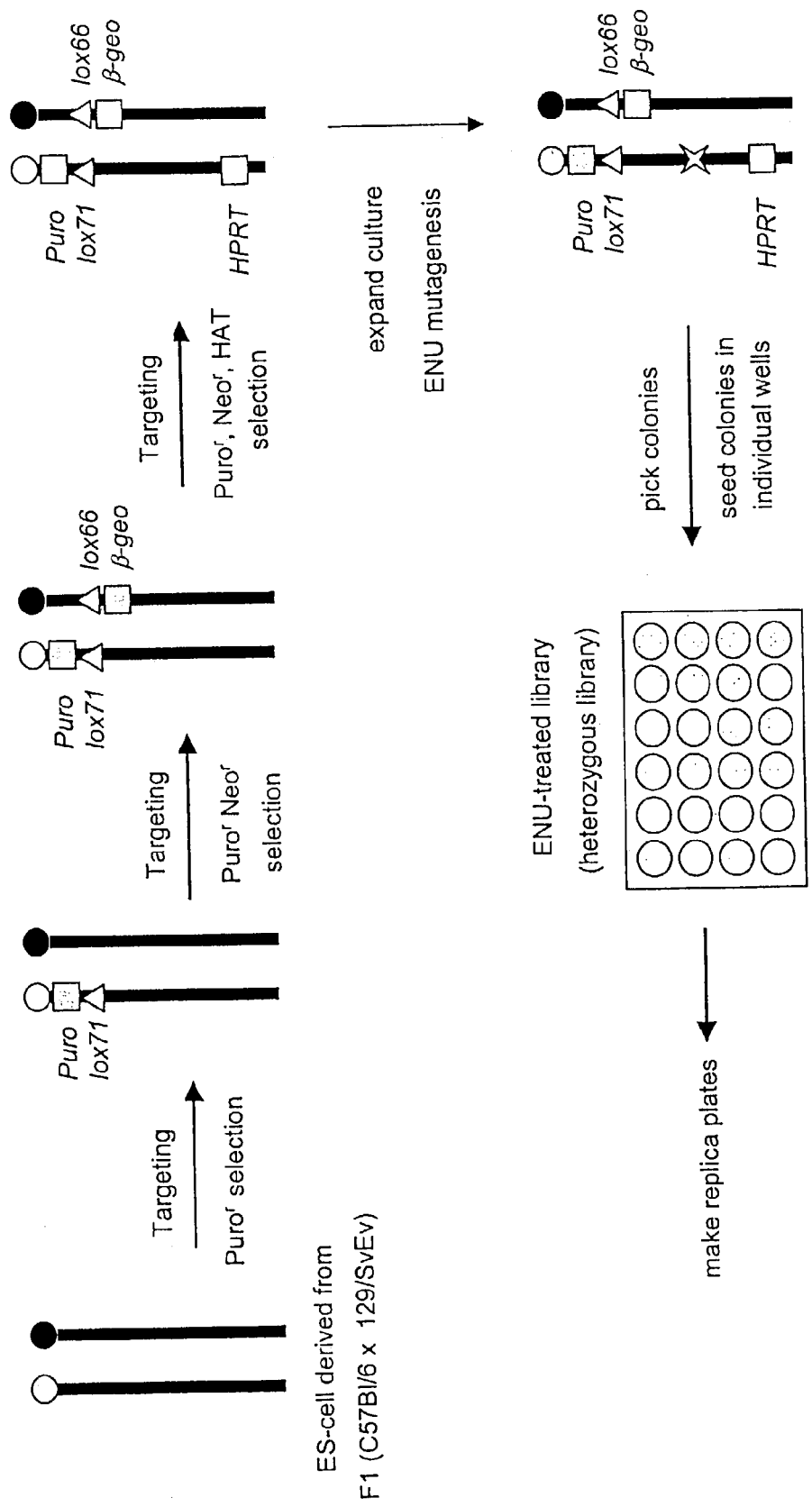
FIG. 4 is a schematic drawing depicting preparation of a marked chromosome pair as described in Example 1, and preparation of a representative embodiment of a heterozygous cellular library as described in Example 2.

The presently claimed subject matter further provides a method for preparing a heterozygous cellular library. In a representative embodiment of the presently claimed subject matter, the method comprises: (a) providing a plurality of isolated cells, wherein each of the plurality of isolated cells comprises a dominant positive selectable marker; and (b) randomly mutagenizing the plurality of isolated cells, whereby a heterozygous cellular library is prepared. Representative methods of the presently claimed subject matter are described in Example 2. See also FIGS. 2 and 4.

Homozygous Cellular Libraries. The term "homozygous cellular library" refers to a randomly mutagenized and homozygosed population of isolated cells. Stated another way, a homozygous cellular library comprises a plurality of isolated cells, wherein each of the cells comprises a homozygous genetic variant.

The term "homozygous genetic variant" refers to a cell comprising one or more genetic modifications that are manifested on each allele. Thus, in a diploid organism, a homozygous genetic modification comprises two copies of a homozygous genetic modification. In accordance with the methods of the presently claimed subject matter, a homozygous genetic variant comprises in one embodiment one or more homozygous genetic modifications on a marked chromosome pair, as described herein below.

The term "homozygosed", as used herein to describe a cellular library of the presently claimed subject matter, refers to a population of isolated cells, wherein each cell comprises one or more homozygous genetic variants.

The presently claimed subject matter further provides a method for making a homozygous cellular library via homozygosing of a heterozygous cellular library. The term "homozygosing" refers to a process whereby cells comprising one or more randomly induced genetic modifications are rendered homozygous at loci comprising the one or more randomly induced genetic modifications.

Figure 3:
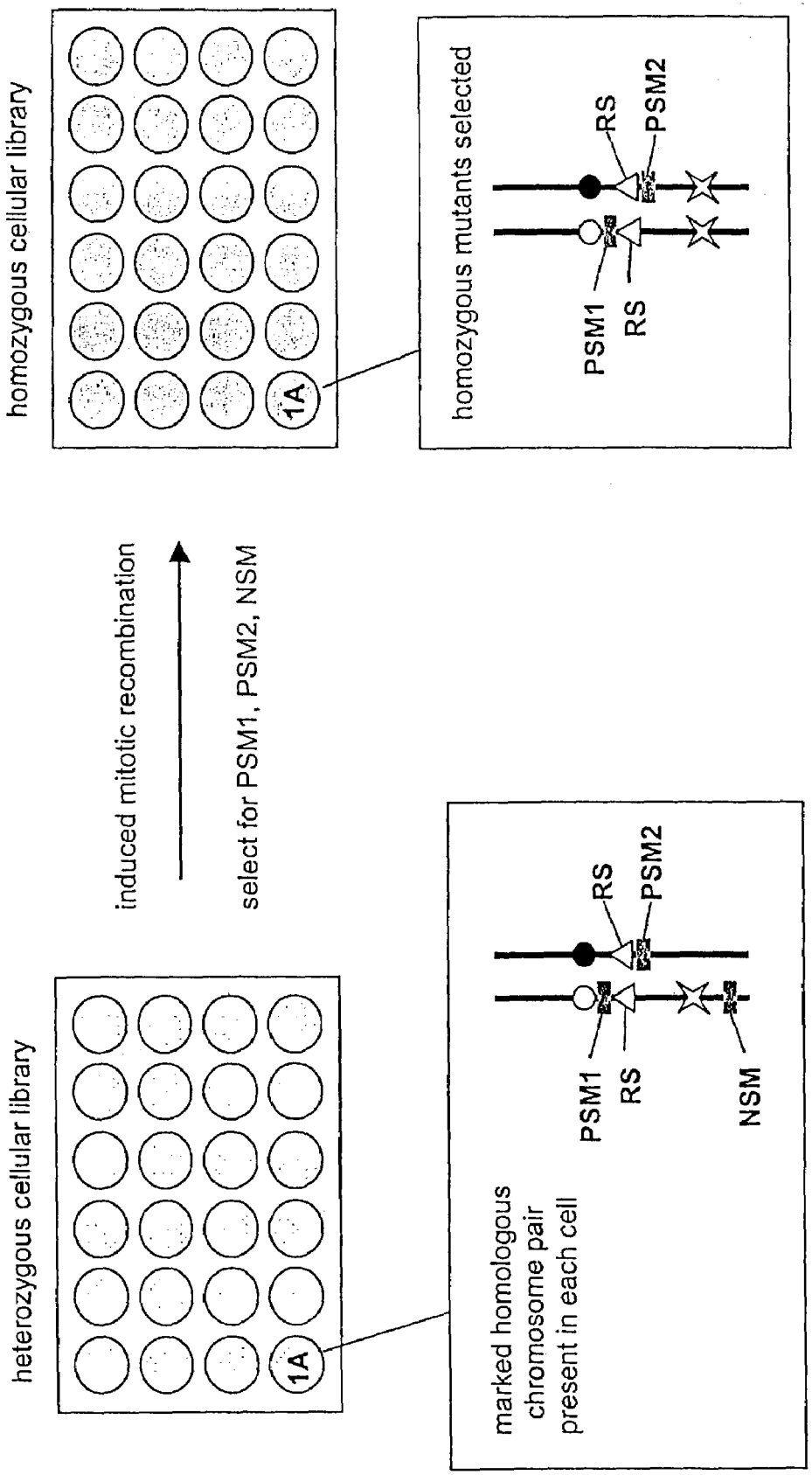
FIG. 3 is a schematic drawing depicting preparation of a homozygous cellular library. PSM1, positive selectable marker 1; PSM2, positive selectable marker 2; NSM, negative selectable marker; ⨉, random mutation; 1A, library position 1A.

In a representative embodiment of the presently claimed subject matter, the method comprises: (a) providing a heterozygous cellular library comprising a plurality of isolated parent cells; (b) inducing site-specific mitotic recombination in the plurality of isolated parent cells; (c) culturing the plurality of isolated parent cells, whereby a population of daughter cells is produced; and (d) selecting daughter cells comprising a homozygous genetic modification, whereby a homozygous cellular library is prepared. Representative methods for preparing a homozygous cellular library are described in Example 4. See also FIGS. 3, 5A, and 5B.

The term "parent cell" is used herein to refer to a cell comprising a cell that can undergo mitotic cell division to thereby produce one or more daughter cells. A population or plurality of parent cells can comprise symmetrically dividing parent cells, asymmetrically dividing parent cells, or a combination thereof.

The term "daughter cell" is used herein to refer to any cell that is produced as a result of a mitotic cell division.

II.A. Cells

A cell of a cellular library can comprise any cell type capable of being cultured, i.e., any cell that can undergo mitotic cell division in culture. Thus, a cell of a cellular library comprises two or more homologous chromosomes (e.g., diploid cells, tetraploid cells, etc.).

A significant advantage of the in vitro phenotyping and gene mapping methods that employ cellular libraries of the presently claimed subject matter is the ability to perform such methods using any cell of interest. Prior to the present disclosure, systematic mutagenesis and gene mapping studies have been substantially confined to model genetic organisms. In contrast, the cellular libraries of the presently claimed subject matter can comprise any cell that can be cultured.

Thus, a cell of a cellular library can comprise a plant cell or an animal cell derived from any species including, but not limited to cells derived from pathogens, domestic animals, agriculturally important animals and plants, etc. In one embodiment of the presently claimed subject matter, cells of a cellular library comprise human cells.

Representative cell types that can be used to prepare a cellular library include but are not limited to differentiated cells and undifferentiated cells, for example stem cells and precursor cells.

The term "differentiated cell" refers to mature cell type. Differentiated cells are typically post-mitotic.

The term "stem cell" refers to a cell that undergoes asymmetric cell division to generate one or more progeny cells and to regenerate itself. Thus, a stem cell is pluripotent in that it can give rise to multiple cell types.

The term "precursor cell" refers to an undifferentiated cell derived from a stem cell, and is not itself a stem cell. A precursor cell can also show pluripotency in that its progeny are capable of differentiating into more than one cell type. A precursor cell does not exhibit self-maintenance. Representative precursor cells include embryonic carcinoma (EC) cells and an embryonic germ (EG) cells.

In one embodiment of the presently claimed subject matter, a cell of a cellular library comprises a totipotent stem cell, which can be used to produce chimeras and non-human cloned organisms for additional phenotypic analysis. For example, an exemplary cell comprises an ES cell, which can itself develop into an entire animal. Other exemplary cells are callus cells and/or cells that can be induced to form callus: cells which have the capacity to regenerate as whole plants.

ES cells can be isolated from any suitable source including, but not limited to the inner cell mass of blastocyst stage embryos (Evans & Kaufman, 1981; Martin, 1981; Magnuson et al., 1982; Doetschman et al., 1988), disaggregated morulae (Eistetter, 1988), and primordial germ cells (Matsui et al., 1992; Resnick et al., 1992).

Methods for isolating and culturing ES cells are known to one skilled in the art. Representative protocols for culture of primate ES cells and mouse ES cells can be found, for example, in Joyner, 2000 and in Tymms & Kola, 2001, among other places. See also U.S. Pat. Nos. 6,190,910, and 6,200,806.

ES cells can also be obtained from agriculturally important animals, including chick, cattle, sheep, goats, rabbits, and mink. Representative isolation and culture methods are described, for example, in PCT International Publication Nos. WO 97/20035 and WO 01/11019, and in U.S. Pat. No. 6,333,192, among other places.

In one embodiment of the presently claimed subject matter, the screening and mapping methods disclosed herein are performed using cellular libraries comprising human ES cells. Representative human ES cells that can be used in accordance with the methods of the presently claimed subject matter include, but are not limited to those human ES cell lines available from ES Cell International (Melbourne, Australia) and from Wisconsin Alumni Research Foundation (Madison, Wis., United States of America). Additional representative human ES cell lines and methods for culturing the same are available from the NIH Human Embryonic Stem Cell Registry, which can be accessed electronically at http://purl.access.gpo.gov/GPO/LPS15792.

Cellular libraries comprising stem cells and precursor cells can be induced to differentiate in vitro. An ES cell can be induced to differentiate in vitro into extraembryonic lineages, somatic cell lineages, or a combination thereof. ES cells can give rise to derivatives of all three germ layers.

Differentiation can be induced prior to, concurrent with, or following random mutagenesis. In one embodiment of the presently claimed subject matter, stem cells are induced to differentiate prior to performing a phenotype assay as described herein below. Thus, cellular libraries can be prepared comprising cell types relevant to a phenotype to be screened, for example any one of cardiomyocytes, smooth muscle cells, adipocytes, hematopoietic progenitors, yolk sac, skeletal myocytes, chondrocytes, endothelial cells, melanocytes, neurons, glia, pancreatic islet cells, and primitive endoderm.

II.B. Marked Chromosomes

The presently claimed subject matter provides cellular libraries comprising a plurality of isolated cells, wherein each of the cells comprises one or more marked chromosomes. As noted herein above, the term "marked chromosome" refers to a chromosome comprising a selectable marker, which is used to select a subpopulation of cells based on expression of the selectable marker, as described further herein below. A selectable marker can be included as part of a recombination cassette, to thereby facilitate selection of a subpopulation following induced mitotic exchange, also described herein below. In one embodiment of the presently claimed subject matter, each of the cells of a cellular library comprises a marked chromosome pair. The term "chromosome pair" as used herein refers to a pair of homologous chromosomes, and further to sets of paired chromosomes. For example, a homologous chromosome pair can comprise a first chromosome and a second homologous chromosome, wherein the first and second chromosomes are each derived from a different parent. A homologous chromosome pair can also comprise a collection of homologous chromosomes present in multiples of two chromosomes (i.e., sets of paired chromosomes), for example as occurs in tetraploid or other polyploid cells.

The term "marked chromosome pair" refers to a homologous chromosome pair wherein each of the homologous chromosomes comprises a selectable marker.

Cells of a cellular library disclosed herein can comprise a single marked chromosome or chromosome pair, or multiple marked chromosomes or chromosome pairs.

Marked chromosomes can be prepared by any suitable method for cellular transformation, whereby a heterologous nucleic acid is incorporated into a host cell genome. The term "heterologous nucleic acid" refers to a nucleic acid molecule that originates from a source foreign to an intended host cell or, if from the same source, is modified from its original form. Thus, a heterologous nucleic acid in a host cell includes a gene that is endogenous to the particular host cell but has been modified, for example by mutagenesis or by isolation from native cis-regulatory sequences. The term "heterologous nucleic acid" also includes non-naturally occurring multiple copies of a native nucleic acid.

In one embodiment of the presently claimed subject matter, marked chromosomes are prepared by gene targeting. The term "gene targeting" generally refers to methods for targeting a heterologous nucleic acid to a predetermined endogenous target DNA sequence in a cell.

The terms "target DNA sequence" and "target site" are used herein interchangeably to refer to DNA intended to be modified by gene targeting. The target DNA sequence can a gene, or part thereof (e.g., an intron, exon, or regulatory sequence) or an intergenic region.

The term "predetermined" refers to a chromosomal site that is selected at the discretion of the practitioner on the basis of known or predicted sequence information, and it is not constrained to specific sequences recognized by site-specific recombinases, as described further herein below. Essentially any chromosomal site for which sequence data is known can be selected as a predetermined site.

The term "targeting DNA" refers to a nucleic acid molecule comprising: (a) a nucleotide sequence to be introduced into the genome; and (b) a nucleotide sequence homologous to the target site. In accordance with the methods of the presently claimed subject matter, a nucleotide sequence to be introduced into the genome includes a selectable marker and/or a recombination cassette to thereby facilitate the preparation of cellular libraries, phenotyping, and mapping methods disclosed herein.

A nucleotide sequence homologous to the target site can be isogenic with the target site to thereby promote the frequency of homologous recombination as described in U.S. Pat. No. 5,789,215.

However, homologous nucleotide sequences that are not isogenic to the target site can also be used. Although it has been demonstrated that the frequency of homologous recombination can be adversely affected by the presence of mismatches between the targeting DNA and the target site, isogenicity is not strictly required. See Sedivy et al., 1999. A nucleotide sequence homologous to the target site is in one embodiment at least about 90% identical to the target site, in another embodiment at least about 95% identical to the target site, and in still another embodiment at least about 99% identical to the target site. Optionally, cellular mismatch repair enzymes can be transitorily inactivated (e.g., by provision of a modulator) to promote recombination of DNA sequences having mismatched bases as described in U.S. Pat. No. 5,965,415.

A targeting DNA can be carried in a vector. The term "vector" is used herein to refer to a nucleic acid molecule having nucleotide sequences that enable its replication in a host cell. A vector can also include nucleic acids to permit ligation of nucleotide sequences within the vector, wherein such nucleic acids are also replicated in a host cell. Representative vectors include plasmids, cosmids, and viral vectors. The term "vector" is also used to describe an expression construct, wherein the expression construct comprises a vector and a nucleic acid operatively inserted with the vector, such that the nucleic acid is expressed. Suitable expression vectors that can be used include, but are not limited to, the following vectors or their derivatives: plasmid and cosmid DNA vectors; viruses such as vaccinia virus or adenovirus, baculovirus vectors, yeast vectors, and bacteriophage vectors (e.g., λ phage).

Vectors can also comprise nucleic acids including expression control elements, such as transcription/translation control signals, origins of replication, polyadenylation signals, internal ribosome entry sites, promoters, enhancers, etc., wherein the control elements are operatively associated with a nucleic acid encoding a gene product. Selection of these and other common vector elements are conventional and many such sequences can be derived from commercially available vectors. See e.g., Sambrook & Russell, 2001, and references cited therein.

Representative protocols for the design of gene targeting vectors can be found, for example, in Hasty et al., 2000; Joyner, 2000; and U.S. Pat. Nos. 5,789,215; 5,859,307; 6,255,113; and 6,319,692; among other places.

Microhomologous recombination in yeast or bacteria, which requires regions of homology as short as 30 base pairs, can be used to facilitate construction of vectors for gene targeting in cells where longer regions of homology to a target site are used for efficient gene targeting. According to this approach, a genomic clone containing the target site in a yeast or bacteria shuttle vector is co-transformed with a targeting DNA into yeast. The targeting DNA can be generated by PCR amplification of the nucleotide sequence to be introduced (e.g., a selectable marker) using primers homologous to the target site. Within the yeast cell, homologous recombination occurs between the targeting DNA and the genomic clone, to thereby produce a targeting DNA comprising longer regions of homology to the target site. See e.g., Zhang et al., 2002; Khrebtukova et al., 1998; and U.S. Pat. Nos. 6,221,647 and 6,069,010.

A targeting vector can be introduced into targeting cells using any suitable method for introducing DNA into cells, including but not limited to microinjection, electroporation, calcium phosphate precipitation, liposome-mediated delivery, viral infection, protoplast fusion, and particle-mediated uptake. Representative methods relevant to transformation of animal cells can be found in, for example, Capecchi, 1980; Potter et al., 1984; Mannino & Gould-Fogerite, 1988; Slilaty & Aposhian, 1983; Rassoulzadegan et al., 1982; Armaleo et al., 1990; and Sambrook & Russell, 2001; among other places.

Optionally, a targeting DNA is co-administered with a recombinase, for example recA, to a target cell to thereby promote a rate of gene targeting. For example, a recombinase protein(s) can be loaded onto a targeting DNA as described in U.S. Pat. No. 6,255,113. To enhance the loading process, a targeting DNA can contain one or more recombinogenic nucleation sequences. A targeting DNA can also be coated with a recombinase protein by pre-incubating the targeting polynucleotide with a recombinase, whereby the recombinase is non-covalently bound to the polynucleotide. See also U.S. Pat. No. 5,780,296.

Selection of cells comprising a homologous integration event is dependent on the design of the targeting vector employed. Representative methods are described in Hasty et al., 2000; Joyner, 2000; and U.S. Pat. Nos. 5,789,215; 5,859,307; 6,255,113; and 6,319,692; among other places.

Representative protocols for gene targeting in cells of non-model animals, including human cells, can be found, for example, in McCreath et al., 2000; Sedivy et al., 1999; Hanson & Sedivy, 1995; among other places. Representative protocols for gene targeting in plant cells can be found, for example, in Risseeuw et al., 1995; Kempin et al., 1997; Offringa & Hooykaas, 1995; and Hanin et al., 2001; among other places.

Representative methods for preparing a marked chromosome pair via gene targeting are described in Example 1. See also FIG. 4.

II.C. Selectable Markers

The term "selectable marker" refers to a peptide or polypeptide whose presence can be readily detected in a heterologous cell when a selective pressure is applied to the cell.

The term "selective pressure" refers to any condition that discerns cells expressing a selectable marker from cells lacking the same selectable marker. In representative embodiments of the presently claimed subject matter, a selective pressure can be applied via provision of a drug (e.g., an antibiotic, a nucleotide analog), provision of an enzymatic substrate (e.g., a chromogenic substrate), exposure to light of an appropriate excitation spectrum, and exposure to an affinity agent or column.

Examples of general types of selectable markers include, but are not limited to: (a) a nucleic acid encoding a gene product that provides resistance against, or otherwise inhibits, toxic compounds; (b) a nucleic acid encoding a gene product that is otherwise lacking in the recipient cell; (c) a nucleic acid encoding a gene product that suppresses an activity of another gene product; (d) a nucleic acid encoding a gene product that modulates an endogenous enzymatic activity; (e) a nucleic acid that can be detected using molecular methods; and (f) a nucleic acid encoding a gene product that is toxic in recipient cells.

In one embodiment of the presently claimed subject matter, a selectable marker comprises an expression-competent selectable marker, wherein a nucleic acid encoding the selectable marker is operatively fused to a promoter.

The term "operatively linked", as used herein, refers to a functional combination between a promoter region and a nucleic acid molecule such that the transcription of the nucleic acid molecule is controlled and regulated by the promoter region. Techniques for operatively linking a promoter region to a nucleic acid molecule are known in the art.

Representative constitutive promoters useful for selectable marker expression in ES cells include a phosphoglycerate kinase I (PGK) promoter, a RNA polymerase II promoter, and a synthetic herpes simplex virus thymidine kinase (HSVtk) promoter (MCI) (Thomas & Capecchi, 1987; Soriano et al., 1991). Representative promoters that direct constitutive expression in plant cells include a Cauliflower Mosaic Virus (CaMV) 35S promoter (Chibbar et al., 1993), an actin promoter (McElroy et al., 1990; McElroy et al., 1991), and a ubiquitin promoter (Norris et al., 1993; Taylor et al., 1993).

An inducible promoter can also be used, for example when expression of the selectable marker induces cell toxicity or death. A representative inducible promoter includes, but is not limited to a chemically inducible promoter (e.g., a promoter regulated by the presence of a small molecule) and a heat-inducible promoter.

Representative chemically-inducible promoters suitable for use in mammalian cells include a metallothionein promoter (Karin et al., 1984; Pellegrini et al., 1994), a tetracycline-responsive promoter (e.g., TET-OFF® and TET-ON® gene expression systems available from Clontech Laboratories, Inc. (Palo Alto, Calif., United States of America), and an ecdysone-inducible promoter (e.g., COMPLETE CONTROL® inducible mammalian expression system available from Stratagene (La Jolla, Calif., United States of America).

Representative inducible promoters suitable for use in plants include the chemically inducible PR-1 promoter (Lebel et al., 1998), an ethanol-inducible promoter (Caddick et al., 1998), and a glucocorticoid inducible promoter (Aoyama & Chua, 1997).

Representative heat-inducible promoters include, but are not limited to heat-responsive elements in heat shock genes (e.g., hsp20–30, hsp27; hsp40, hsp60, hsp70, and hsp90). See Easton et al., 2000; Csermely et al., 1998; Ohtsuka & Hata, 2000; and references cited therein.

In another embodiment of the presently claimed subject matter, a selectable marker is targeted to a position in the genome such that expression of the selectable marker is controlled by an endogenous gene. See e.g., Wolfgang & Gossler, 2000; Hanks et al., 1995.

Selectable markers employed in the methods of the presently claimed subject matter can confer dominant or recessive selectable phenotypes based on the host cell genotype. The term "dominant", as used herein to describe a selectable marker, refers to a selectable marker that it is effective in a naturally occurring cell. The term "recessive", as used herein to describe a selectable marker, refers to a marker that can be selected when expressed in cells that lack the corresponding endogenous gene, for example by spontaneous, induced, or targeted mutation. A variety of selectable markers have been described which act in either a dominant or recessive context, as noted herein below.

The term "selectable marker" encompasses positive selectable markers and negative selectable markers. Positive selectable markers and negative selectable markers are chosen as suited for a particular application. One skilled in the art can readily select an appropriate marker and selective pressure to enable selection of a desired subpopulation.

The term "positive selectable marker" refers to a marker that confers selection of cells expressing the marker in the presence of a selective pressure.

The term "negative selectable marker" refers to a marker that confers selection of cells lacking the marker in the presence of a selective pressure.

Some markers behave as positive selectable markers or negative selectable markers, depending on the selective pressure employed. For example, HPRT-positive cells are selected by growth in HAT (hypoxanthine/aminopterin/thymidine) medium. HPRT-negative cells are selected by growth in 6-thioguanine (6-TG).

A selectable marker can also be used to positively select and negatively select cells comprising the marker when subjected to a same selective pressure. For example, cells expressing a fluorescent selectable marker (e.g., GFP, CFP, YFP, etc.) can be alternately recovered using a fluorescent-activated cell sorter (FACS) such as an EPICS® cell sorter available from Coulter Electronics, Inc. (Hialeah, Fla., United States of America).

The term "selectable marker" also encompasses a fusion protein comprising multiple selectable markers. For example, the β-geo fusion protein comprises a lacZ gene fused in-frame to a neo gene and shows both β-galactosidase activity and G418 resistance (Friedrich & Soriano, 1991). Additional selectable markers comprising fusion proteins are described in Abbate et al., 2001; Chen & Bradley, 2000; Oh et al., 2001. In one embodiment, the combination of markers permits selection in different settings, for example, both in vitro and in vivo.

A selectable marker can be introduced at a particular locus or chromosomal position as best suited for a particular application. Exemplary positions of a marker include positions at or near the extremities of a chromosome arm. The term "distal chromosome marker" is used herein to describe a marker that is introduced at or near a distal tip of a chromosome arm. The term "centromeric chromosome marker" is used herein to describe a marker that is introduced at or near centromeric chromatin of a chromosome arm.

For preparation of a heterogeneous cellular library, wherein the heterogeneous cellular library will be used for phenotyping and mapping of dominant phenotypes, a selectable marker can comprise a positive selectable marker. Thus, a heterozygous cellular library can comprise a randomly mutagenized population of cells, wherein each of the cells comprises one or more marked chromosome comprising a dominant, positive selectable marker. In one embodiment, cells of a heterozygous cellular library comprise a different positive selectable marker on each of multiple marked chromosomes.

Representative dominant, positive selectable markers for mammalian cells include the bacterial aminoglycoside 3' phosphotransferase gene (neo), which confers resistance to the drug G418 in mammalian cells; the bacterial puromycin-N-acetyltransferase gene (puro), which confers resistance to the antibiotic puromycin; the bacterial hygromycin G phosphotransferase gene (hyg), which confers resistance to the antibiotic hygromycin; the bacterial blasticidin S deaminase gene (bsr); the bacterial xanthine-guanine phosphoribosyl transferase gene (gpt), which confers the ability to grow in the presence of mycophenolic acid; and the bacterial Sh ble gene (zeo), which confers resistance to the antibiotics phleomycin and ZEOCIN™ (Invitrogen Corp., Carlsbad, Calif., United States of America). In addition, the X-linked hypoxanthine-guanine phosphoribosyl transferase (hprt) gene serves as a dominant marker in male cells.

Representative positive selectable markers useful in plant cells include herbicide resistance genes and antibiotic resistance genes. Selection markers used routinely in transformation include the nptII gene, which confers resistance to kanamycin and related antibiotics (Vieira & Messing, 1982); the bar gene, which confers resistance to the herbicide phosphinothricin (Vieira & Messing, 1982); the hph gene, which confers resistance to the antibiotic hygromycin (Blochlinger & Diggelmann, 1984); the dhfr gene, which confers resistance to methatrexate (Bourouis & Jarry, 1983); the EPSPS gene, which confers resistance to glyphosate (U.S. Pat. Nos. 4,940,935 and 5,188,642); the mannose-6-phosphate isomerase gene, which provides the ability to metabolize mannose (U.S. Pat. Nos. 5,767,378 and 5,994,629); and the doubly mutant protoporphyrinogen (PPO) gene, which confers resistance to the herbicide BUTAFENACIL™ (Syngenta Biotechnology Inc., Research Triangle Park, N.C., United States of America; Hanin et al., 2001).

Additional representative dominant, positive selectable markers include fluorescent proteins (e.g., GFP, CFP, YFP), and enzymes that can catalyze formation of a fluorescent product. These selectable markers enable sorting of cells based on detectable fluorescence, for example using a fluorescence-activated cell sorter.

A dominant, positive selectable marker can also comprise a peptide or polypeptide located on the cell surface, as described in PCT International Publication No. WO 95/06723. Cell surface marker polypeptides include membranous polypeptides such as LNGFR (low-affinity nerve growth factor receptor), CD24, and LDLR (low-density lipoprotein receptor). Also included are extracellularly presented fragments of membranous polypeptides. In one embodiment, such fragments comprise ligand-binding or antigenic fragments to enable selection. Similarly, a peptide selectable marker can comprise a peptide (e.g., $His_6$) targeted to the cell surface using recombinant techniques known to one skilled in the art. In one embodiment, a peptide or polypeptide selectable marker is not endogenously expressed in the cells of a cellular library. Selection of cells comprising an extracellularly presented peptide or polypeptide marker can be accomplished by use of a binding partner (e.g., an antibody, an endogenous ligand, a synthetic ligand, or any other binding partner) that specifically binds to the marker. See e.g., PCT International Publication No. WO/95/06723 and U.S. Pat. No. 6,284,541.

For preparation of a heterozygous cellular library, wherein the library will be used to prepare a homozygous cellular library, each of the cells of the cellular library can comprise a marked chromosome pair comprising: (a) a distal selectable marker; and (b) an allelic pair of recombination cassettes, as described further herein below. Optionally, each recombination cassette of the pair comprises a dominant, positive selectable marker (e.g., any of those selectable markers noted herein above).

In another embodiment, each of the cells of the cellular library comprises a marked chromosome pair comprising: (a) a first distal selectable marker on a first chromosome; (b) a second distal selectable marker on a second homologous chromosome; and (c) an allelic pair of recombination cassettes.

A distal selectable marker can enable selection of homozygous chromosomes following induced mitotic recombination of a cell comprising the marked chromosome pair. Thus, a distal selectable marker comprises in one embodiment: (a) a dominant, negative selectable marker; or (b) a recessive, positive selectable marker.

In one embodiment of the presently claimed subject matter, a marked chromosome pair comprises a recessive, positive selectable marker at a distal position on a first chromosome, and a dominant, negative selectable marker at a distal position on a second homologous chromosome, thereby permitting recovery of genetic modifications induced on each chromosome of the marked chromosome pair.

Representative dominant, negative selectable markers that confer cytotoxicity include, but are not limited to gpt, which confers cytotoxicity in the presence of (6-thioxanthine) 6-TX; and HSVtk, which confers cytotoxicity in the presence of gancyclovir or 2'-fluoro-2'-deoxy-1-β-D-arabinofuranosyl-5-iodo-uracil (FIAU). Expression of the dominant, negative selectable marker encoding diphtheria toxin A fragment operates in the absence of an applied selective pressure.

A dominant, negative selection marker can also comprise a peptide or polypeptide that is presented on the cell surface in analogy to peptide markers described herein above as dominant, positive selectable markers. See U.S. Pat. No. 6,284,541.

Recessive, positive selectable markers are used when expressed in a mutant background devoid of the marker gene function. Representative recessive, positive selectable markers include but are not limited to thymidine kinase (tk), Herpes simplex thymidine kinase (HSVtk), carbamoylphosphate synthetase 2/aspartate transcarbamylase/dihydroorotase (CAD), hprt or an hprt minigene (Reid et al., 1990).

II.D. In Vitro Mutagenesis

The term "mutagenizing" is used herein to refer to a method for inducing one or more genetic modifications in cellular nucleic acid material.

The terms "genetic modification" and "mutation" each refer to any alteration of DNA that to a form that is different than its naturally occurring form. Representative gene modifications include nucleotide insertions, deletions, substitutions, and combinations thereof, and can be as small as a single base or as large as tens of thousands of bases. Thus, the term "genetic modification" encompasses inversions of a nucleotide sequence and other chromosomal rearrangements, whereby the position or orientation of DNA comprising a region of a chromosome is altered. A chromosomal rearrangement can comprise an intrachromosomal rearrangement or an interchromosomal rearrangement.

In one embodiment, the mutagenizing methods employed in the presently claimed subject matter are substantially random such that a genetic modification can occur at any available nucleotide position within the nucleic acid material to be mutagenized. Stated another way, in one embodiment the mutagenizing does not show a preference or increased frequency of occurrence at particular nucleotide sequences.

The methods of the presently claimed subject matter can employ any mutagenic agent including, but not limited to ultraviolet light, X-ray radiation, gamma radiation, N-ethyl-N-nitrosourea (ENU), methyinitrosourea (MNU), procarbazine (PRC), triethylene melamine (TEM), acrylamide monomer (AA), chlorambucil( CHL), melphalan (MLP), cyclophosphamide (CPP), diethyl sulfate (DES), ethyl methane sulfonate (EMS), methyl methane sulfonate (MMS), 6-mercaptopurine (6-MP), mitomycin-C (MMC), N-methyl-N'-nitro-N-nitrosoguanidine (MNNG), $^3H_2O$, and urethane (UR). See e.g., Rinchik, 1991; Marker et al., 1997; and Russell, 1990. Additional mutagenic agents are described at http://dir.niehs.nih.gov/dirtb/dirrtg/chemicalsstudiedindex2.htm.

In one embodiment of the presently claimed subject matter, ENU is employed as a mutagenic agent. ENU can efficiently produce point mutations and, less frequently, small deletions at sites throughout the genome. These types of genetic modifications can lead to reduced or lost gene function (including dominant negative gene function), up-regulated gene function, and altered or new gene function.

The term "mutagenizing" also encompasses a method for altering (e.g., by targeted mutation) or modulating a cell function, to thereby enhance a rate, quality, or extent of mutagenesis. For example, a cell can be altered or modulated to thereby be dysfunctional or deficient in DNA repair, mutagen metabolism, mutagen sensitivity, genomic stability, or combinations thereof.

Thus, disruption of gene functions that normally maintain genomic stability can be used to enhance mutagenesis. Representative targets of disruption include, but are not limited to DNA ligase I (Bentley et al., 2002) and casein kinase I (U.S. Pat. No. 6,060,296).

The frequency of genetic modification upon exposure to one or more mutagenic agents can be modulated by varying dose and/or repetition of treatment, and can be tailored for a particular application. For example, if subsequent phenotypic screening involves identification of a rare drug resistance phenotype, then a frequency of genetic modification can be selected whereby multiple mutations are induced on each chromosome. Similarly, if the library will be used to screen for a more general differentiation phenotype, then the dose and administration of mutagen can be varied to generate a relatively fewer number of genetic modifications per chromosome. In one embodiment, the treatment dose and regimen does not induce substantial cytotoxicity.

II.E. Induced Mitotic Recombination

The presently claimed subject matter further provides methods for homozygosing a heterozygous library of the presently claimed subject matter via induced mitotic recombination. In a representative embodiment of the presently claimed subject matter, the method comprises: (a) providing a heterozygous cellular library comprising a plurality of isolated parent cells; (b) inducing site-specific mitotic recombination in the plurality of isolated parent cells; (c) culturing the plurality of isolated parent cells, whereby a population of daughter cells is produced; and (d) selecting daughter cells comprising a homozygous genetic modification, whereby a homozygous cellular library is prepared.

The term "recombination" refers to a process wherein chromosomes are broken and rejoined in new combinations. The term "mitotic recombination" refers to recombination between or among homologous chromosomes during mitotic cell division.

The term "induced", as used herein to describe a type of mitotic recombination, refers to a process whereby mitotic recombination is elicited at predetermined chromosomal sites via provision of a site-specific recombinase. In one embodiment, induced mitotic recombination results in exchange of substantially the entire region of a marked chromosome arm with the allelic region of a marked homologous chromosome arm, as described further herein below. Thus, the term "inducing mitotic recombination" refers to provision of a site-specific recombinase to a cell, whereby mitotic recombination is induced.

The term "chromosomal site", as used herein to describe a site at which mitotic recombination is induced, refers to a position on a chromosome characterized by a unique nucleotide sequence that is recognized by a site-specific recombinase. A chromosomal site for induced mitotic recombination can be predetermined by modifying genomic sequence at a given site to include a recombination site. Such modifications can be made using gene targeting methods, as described herein above. See also Example 1.

A chromosomal site for site-specific mitotic recombination is also referred to herein as a "recombination site." Representative recombination sites for include lox, FRT, and att sites, which mediate mitotic recombination via Cre recombinase, FLP recombinase, and Int recombinase, respectively, as described further herein below.

In one embodiment, a combination of a site-specific recombinase and recombination sites is selected such that a first recombination event is stable, thereby favoring recovery of homozygous chromosomes. A first recombination event is referred to as "stable" when it does not readily recombine again. Stated another way, the recombination sites are excision-resistant following a first recombination event.

Stability of a first recombination can be favored by: (a) recombination sites that recombine to generate a recombination site that resists excision; (b) site-specific recombinases that display compromised excision functions; (c) a presence or absence of modulators of a site-specific recombinase, for example accessory proteins of a site-specific recombinase; and (d) combinations thereof.

For example, the λ Int recombinase, when provided in the absence of the Xis accessory protein, mediates recombination at attP and attB sites that is essentially irreversible (Thorpe & Smith, 1998). As another example, Cre-induced recombination at mutant lox sites lox66 and lox71 generates a modified lox site that is unable to subsequently recombine despite the presence of Cre.

Site-Specific Recombinases. The term "recombinase" generally refers to an enzyme that catalyzes recombination.

The term "site-specific", as used herein to describe a type of recombinase or a type of recombination, refers to a process of breaking and joining chromosomes at prescribed positions, which are referred to herein as "recombination sites." In accordance with the methods of the presently claimed subject matter, a site-specific recombinase mediates recombination at prescribed sites on homologous chromosomes.

Any suitable site-specific recombinase can be used to induce mitotic exchange in a cell of a cellular library, provided that the chromosomes of the cell comprise recombination sites recognized by the site-specific recombinase of choice.

Thus, a site-specific recombinase comprises in one embodiment a resolvase-type recombinase (Stark et al., 1989; Maeser & Kahmann, 1991; Oram et al., 1995) that mediates intrachromosomal recombination. In another embodiment, a site-specific recombinase employed in the methods of the presently claimed subject matter comprises an integrase-type recombinase including, but not limited to prokaryotic plasmid recombinases, yeast plasmid recombinases, bacterial recombinases of the Xer and Fim families, and phage recombinases (Esposito & Scocca, 1997; Grainge & Jayaram, 1999).

Representative integrase-type recombinases include but are not limited to an Int recombinase, including those derived from phage phiC31 (Groth et al., 2000; Thyagarajan et al., 2001), phage R4 (Olivares et al., 2001), or from phage HK022 (Kolot et al., 1999); a Cre recombinase (Sauer & Henderson, 1988; Nagy, 2000), a FLP recombinase (Fiering et al., 1993; Sadowski, 1995; Seibler et al., 1998), and an integrase-type recombinase from bovine leukemia virus (Tanaka et al., 1998).

In one embodiment of the presently claimed subject matter, a site-specific recombinase used in the disclosed methods comprises a Cre recombinase. Representative Cre recombinases can comprise amino acid sequences disclosed as any one of GenBank Accession Nos. P06956, CAD22449, CAD22450, CAD22957, CAD22958, CAD22959, CAC51201, AAL31698, and JC7213, which are herein incorporated by reference in their entirety.

The term "site-specific recombinase" also encompasses functional variants, fragments, and fusion proteins of any of the foregoing recombinases. Thus, a recombinase used in accordance with the methods of the presently claimed subject matter can also comprise a recombinase that has been mutagenized to produce a recombinase with altered properties as desired for a particular application. For example, a site-specific recombinase can comprise enhanced FLP (FLPe), which was selected following a protein evolution strategy to improve thermolability of FLP (Buchholz et al., 1998; Schaft et al., 2001). See also Sclimenti et al., 2001. A site-specific recombinase can also be modified to improve expression and inducibility, for example by optimization of codon usage as described in Koresawa et al., 2000; in European Patent 1170354; and in PCT International Publication No. WO 02/04609.

In one embodiment, a site-specific recombinase employed in the methods of the presently claimed subject matter can mediate recombination in the absence of accessory factors. However, additional factors that contribute to or modulate a recombinase activity can be co-administered with a recombinase of the presently claimed subject matter. For example, integrative recombination induced by bacteriophage λ Int recombinase involves the integration host factor (IHF) protein (Landy, 1993). To induce mitotic recombination in cells of a heterozygous cellular library of the presently claimed subject matter, a site-specific recombinase is provided to cells of the library in any manner sufficient to induce mitotic recombination. In one embodiment, the method is amenable to high-throughput formats.

In one embodiment of the presently claimed subject matter, cells are transfected with a nucleic acid molecule encoding a site-specific recombinase, whereby the site-specific recombinase is expressed and can mediate mitotic recombination. The transfected nucleic acid can be maintained as an extrachromosomal construct or can be stably integrated into the genome. Any suitable method for the introduction of a nucleic acid can be used, including transfection, microinjection, electroporation, infection with viral vectors, microparticle bombardment, etc. A representative protocol for introducing a nucleic acid molecule encoding a recombinase into a cell by electroporation is described in Liu et al., 2002. As another example, representative protocols for infecting a cell with a viral vector encoding a site-specific recombinase are described in Kanegae et al., 1995 and in Rinaldi et al., 1999.

In one embodiment of the presently claimed subject matter, a polypeptide comprising a site-specific recombinase is provided to cells of a cellular library. For entry into cells, a site-specific recombinase comprises in one embodiment a cell-permeable, site-specific recombinase.

The term "cell permeable", as used herein to describe a site-specific DNA recombinase, refers to a recombinase that is able to transduce cell membranes. While not intended to be limited to any particular theory of operation, the translocation can occur in a receptor-independent and transporter-independent manner.

When applied exogenously to a cell, a cell-permeable recombinase can enter the cell and mediate mitotic recombination of cellular DNA. Following a temporal duration sufficient for mitotic recombination, a cell-permeable recombinase can be removed by washing the cells in culture medium lacking the recombinase. Thus, methods for chromosomal exchange employing a cell-permeable recombinase include desirable features for controlling recombinase activity in a cell.

A cell-permeable recombinase can comprise a fusion polypeptide comprising a recombinase (e.g., any one of the site-specific recombinases identified herein above) fused to a membrane translocating sequence (MTS). For example, a cell-permeable recombinase can comprise a Cre recombinase fused to the MTS of Kaposi fibroblast growth factor as described by Jo et al., 2001. See also Example 4.

The term "membrane translocation sequence" generally refers to an amino acid sequence that, in the context of a larger protein, mediates translocation of the protein across a membrane. Representative membrane translocation sequences that can be used to construct a cell-permeable recombinase include, but are not limited to MTSs of fibroblast growth factors (Lin et al., 1995; Tarantini et al., 1998; Keresztes & Boonstra, 1999), lactoferrin (He & Furmanski, 1995), VP22 (Elliott & O'Hare, 1997), ANTP (Joliot et al., 1991), TAT (Frankel & Pabo, 1988; Green & Loewenstein, 1988; Schwarze et al., 1999), engrailed (Joliot et al., 1998), and Hoxa-5 (Chatelin et al., 1996). Synthetic MTSs can also be used to construct a cell-permeable recombinase (Oehlke et al., 1998; Pooga et al., 1998a; Pooga et al., 1998b; Scheller et al., 1999).

Representative methods and considerations for constructing a fusion protein comprising a MST can be found in, for example, Derossi et al., 1998; Lindgren et al., 2000; Prochiantz, 2000; and the references cited herein above, among other places.

Recombination Cassettes. To provide for induced mitotic recombination, a heterozygous cellular library can comprise a marked chromosome pair comprising: (a) a first chromosome comprising a first recombination cassette; and (b) a second homologous chromosome comprising a second recombination cassette, wherein the first recombination cassette and the second recombination cassette are allelic.

The term "recombination cassette" refers to a nucleic acid molecule comprising a site for site-specific recombination, i.e. a nucleotide sequence at which a site-specific recombinase mediates strand breakage and rejoining. Representative recombination sites include a lox site, an FRT site, and an att site, as described further herein below.

The term "allelic" refers to a same chromosomal position on homologous chromosomes. For example, a first position is allelic to a second position, wherein a first position is located within a gene or intergenic region, and wherein a second position is located within the same gene or intergenic region on a homologous chromosome.

The term "lox site" refers to a nucleotide sequence that mediates mitotic recombination by a Cre recombinase, for example a naturally occurring lox site, loxP. A lox site typically comprises an about 34 base pair sequence that includes a core spacer sequence of about 8 base pairs and a pair of palindromic sequences that flank the core spacer, each palindromic region comprising about 8 base pairs to about 13 base pairs. See Hoess et al., 1982.

The term "FRT site" refers to a nucleotide sequence that mediates mitotic recombination by a FLP recombinase. An FRT site is similar to a lox site, comprising a minimal sequence of about 34 base pair sequence that includes a core spacer sequence of about 8 base pairs and a pair of palindromic sequences that flank the core spacer, each palindromic region comprising about 8 base pairs to about 13 base pairs (McLeod et al., 1986). Typically, a palindromic sequence of an FRT site includes a pyrimidine tract, and a spacer region includes a predominance of AT base pairs (Umlauf & Cox, 1988). This minimal sequence is also flanked on one side by an about 13 base pair inverted repeat, which can promote the efficiency of recombination (Jayaram, 1985).

A lox site and an FRT site each comprise a directionality, which is defined by the asymmetry of the core spacer. The outcome of recombination reactions depends on the relative orientation of the two recombining sites. Conventions for describing the directionality of a lox site and an FRT site are described in Snaith et al., 1995.

In accordance with a representative method of the presently claimed subject matter, a marked chromosome pair of a cell of a cellular library can comprise a pair of lox sites or a pair of FRT sites, wherein each pair of recombination sites comprises a same orientation. See FIGS. 3, 4, and 5B.

The term "att site" refers to a nucleotide sequence that mediates mitotic recombination by an Int recombinase. Representative att sites include attB, attP, attL, and attR. attB is an about 25 base pair sequence containing two 9 base pair core-type Int binding sites and a 7 base pair overlap region. attP is an about 240 base pair sequence containing "coretype" Int binding sites, "arm-type" Int binding sites, and binding sites for accessory recombination proteins. See Landy, 1989. Phage Int recombinases catalyze recombination between an attB site and an attP site. Recombination results in hybrid sites attL and attR, which are refractory to further recombination unless a excisionase protein is supplied (Thorpe & Smith, 1998). The terms "lox site", "FRT site", and "att site" also encompass recombination sites that have been modified from their naturally occurring sequence and which mediate recombination by a Cre recombinase, a FLP recombinase, or an lnt recombinase, respectively. For example, a recombination site can be modified to enhance specificity of recombination, efficiency of recombination, and stability of a recombination event. A modified recombination site can be generated using standard techniques in the field, including but not limited to chemical synthesis of a modified site and mutagenesis. See e.g., Lee & Saito, 1998; Schlake & Bode, 1994; and PCT International Publication Nos. WO 01/23545 and WO 99/25851.

As noted herein above, recombination sites can be selected to favor stability of a first recombination event. Thus, in one embodiment of the presently claimed subject matter, a cell of a cellular library comprises a marked chromosome comprising a first recombination cassette and a second allelic recombination cassette, wherein the first recombination cassette comprises a lox66 site, and wherein the second recombination cassette comprises a lox71 site. Lox66 recombines with lox71 to produce a mutant lox site that will not recombine with itself or a wild type loxP site (Albert et al., 1995; Araki et al., 1997).

In another embodiment of the presently claimed subject matter, a cell of a cellular library comprises a marked chromosome comprising a first recombination cassette and a second allelic recombination cassette, wherein the first recombination cassette comprises an attB site, and wherein the second recombination cassette comprises an attP site.

A recombination cassette used in accordance with the methods of the presently claimed subject matter can further comprise a plurality of recombination sites to thereby promote the frequency of recombination. As one example, a recombination cassette can comprise a pair of recombinase sites that flank an arbitrary intervening sequence. See e.g., Liu et al., 2002.

Similarly, a marked chromosome can further comprise multiple recombination cassettes in substantially close proximity on a chromosome to thereby promote the efficiency of recombination. For example, two or more recombination cassettes can be located within in one embodiment a region spanning about 100 kilobases (kb), in another embodiment a region spanning about 10 kb, in another embodiment a region spanning about 1 kb, and in still another embodiment a region spanning about 100 base pairs.

A recombination cassette can optionally comprise a dominant, positive selectable marker such that the presence of the selectable marker indicates the presence of a chromosomal site for induced mitotic recombination. A selectable marker included in a recombination cassette also facilitates selection of cells comprising a homozygous mutation following induced mitotic recombination.

Thus, a cell of a heterozygous library useful for preparing a homozygous cellular library comprises in one embodiment a marked chromosome pair comprising: (a) a first recombination cassette, wherein the first recombination cassette comprises a first recombination site and a first selectable marker proximal to the first recombination site; and (b) a second recombination cassette, wherein the second recombination site comprises a second recombination site and a second selectable marker distal to the second recombination site.

The terms "proximal" and "distal" are used herein according to convention in the art to describe relative positions along a chromosome arm. The term "proximal" refers to a first position that is closer to a centromere when compared to a second position on a same chromosome arm. Conversely, the term "distal" refers to a first position that is further from a centromere, or closer to a chromosomal tip, when compared to a second position on a same chromosome arm.

To optimize the size of chromosomal regions that are exchanged during induced mitotic recombination, recombination cassettes are located in one embodiment at chromosomal positions that are substantially close to the centromere, also referred to herein as a "centromeric" position. The phrase "substantially close", as used herein to describe to a proximity of a recombination cassette to a centromere, refers to a chromosomal distance in one embodiment less than about 50% of a chromosome arm, in another embodiment less than about 25% of a chromosome arm, in another embodiment less than about 10% of a chromosome arm, in another embodiment less than about 5% of a chromosome arm, in another embodiment less than about 1% of a chromosome arm, and in still another embodiment less than about 0.1% of a chromosome arm. A chromosomal distance can be measured, for example in map units, as described further herein below under the heading "Gene Mapping". Stated another way, the phrase "substantially close" can refer to a position within or adjacent to a satellite DNA sequence of centromeric chromatin (e.g., an alphoid).

The frequency of induced mitotic recombination can vary according to the chromosomal location of the recombination sites. See e.g., Herault et al., 1998 and Liu et al., 2002. Thus, a recombination cassette employed in the methods of the presently claimed subject matter can be introduced at a chromosomal site (e.g., by gene targeting) that mediates induced mitotic recombination at a frequency of in one embodiment at least about 0.1%, in another embodiment at least about 1%, in another embodiment at least about 10%, and in yet another embodiment at least about 20%. As required, position-dependent frequency of induced mitotic recombination can be empirically determined and using standard methods in the art.

III. In Vitro Phenotyping

The presently claimed subject matter further provides methods for screening cellular libraries prepared as disclosed herein to assess a phenotype of interest. Replica plates of a heterozygous cellular library or a homozygous cellular library can be prepared, such that a single library can be evaluated in multiple, different phenotypic assays. The in vitro phenotyping methods of the presently claimed subject matter advantageously eliminate the requirement for generation of whole organisms in which to evaluate gene function.

The term "phenotype" refers to any observable property of an organism that is dependent upon the genome of the organism. A phenotype can be further characterized as modulated by a non-genetic factor, an interaction between two or more non-genetic factors, an interaction between a genetic locus and a non-genetic factor, or an interaction between two or more genetic loci and non-genetic factors. A non-genetic factor comprises an environmental condition or exposure, for example a habitat condition, a level of activity or exercise, diet, a drug treatment, and combinations thereof.

The term "phenotype", alternately expressed herein as "phenotyping", also refers to a method for assaying a phenotype. A phenotyping method is in one embodiment amenable to high-throughput formats such that a phenotype of each of the cells of the library is rapidly assessed. Cells that display a phenotype of interest can be selected, and subsequent phenotyping can be performed in chimeric or cloned organisms, as described herein below.

PCT International Publication No. WO 99/67361 to Woychik et al. discloses a method for screening a heterozygous cellular library by detecting the occurrence of mutations in a gene of interest. For example, a gene of interest can be amplified by PCR, and the sequence of the amplified product can be analyzed to identify genetic modifications. Thus, a screen conducted according to the method of Woychik et al. requires determination of a mutant genotype.

In contrast to Woychik et al., the presently claimed subject matter provides that cellular libraries of the presently claimed subject matter can be screened based on a resulting phenotype, which can be caused by genetic modification of any locus segregating on a marked chromosome. A phenotypic screening approach as disclosed herein also enables discovery of interacting loci that contribute to a phenotype (e.g., in the case of oligogenic and complex traits).

In one embodiment of the presently claimed subject matter, a screening method employs a heterozygous cellular library, wherein each of the cells of the cellular library comprises a marked chromosome. Phenotyping of a heterozygous cellular library is used to identify dominant mutations that confer a phenotype of interest.

In another embodiment of the presently claimed subject matter, a screening method employs a homozygous cellular library. In this case, a phenotypic screening of the library identifies recessive mutations that confer a phenotype of interest.

In accordance with the presently claimed subject matter, in vitro phenotyping methods of the presently claimed subject matter are conducted in multi-well plate format. For example, a replica of a cellular library maintained in a multi-well plate can be used directly for phenotyping assays.

The cellular libraries of the presently claimed subject matter can be screened in any microplate format, including a 96-well microplate as well as higher density formats such as 384-well, 560-well, 864-well, 1,536-well, and 3,456-well microplates. Representative protocols and instrumentation for conducting cell-based assays in high density formats are described in, for example, Kolb & Neumann, 1997; Dias et al., 1998; Maffia et al., 1999; and Mere et al., 1999, among other places.

The disclosed serial process of generating a cellular library, phenotyping the library, and selecting one or more genetic variants that display a phenotype of interest, can be repeated as desired to uncover multiple, interacting genetic loci. For example, a mutant cell of a homozygous cellular library, which bears a modification of a first genetic locus that confers a phenotype of interest, can further be expanded and mutagenized as described herein above. The resulting derivative cellular library can then be used to perform a same phenotyping assay, whereby a second, interacting genetic locus is identified.

III.A. In Vitro Differentiation

As noted herein above, a cellular library of the presently claimed subject matter can comprise precursor cells or stem cells, which are induced to differentiate prior to conducting a phenotyping assay. Differentiation of a precursor cell or a stem cell can be induced by any suitable method including, but not limited to provision of growth factors, provision of an inducing substrate, and co-culture with other cell types In one embodiment, heterogeneity among the differentiated cells is limited, such that the differentiated population is substantially a single cell type.

For example, mammalian ES cells can be induced to develop as differentiated cardiocytes (Wobus et al., 1991; Maltsev et al., 1993; Miller-Hance et al., 1993; Maltsev et al., 1994; Wobus et al., 1997), myocytes (Miller-Hance et al., 1993; Rohwedel et al., 1994; Rose et al., 1994), neural cells (Bain et al., 1995; Fraichard et al., 1995; Strubing et al., 1995; Okabe et al., 1996), hematopoietic cells (Wiles & Keller, 1991; Hole & Smith, 1994; Keller, 1995), adipocytes (Dani et al., 1997), epithelial cells (Bagutti et al., 1996), endothelial cells (Risau et al., 1988), and vascular smooth muscle cells (Risau et al., 1988; Weitzer et al., 1995; Drab et al., 1997).

Methods for inducing cellular differentiation in vitro are known in the art. Representative protocols can be found in the references to particular cell types cited herein above. See also U.S. Pat. Nos. 6,322,784; 6,294,346; 6,033,906; 6,093,531; 6,129,911; 6,117,675; and 6,001,654; and PCT International Publication Nos. WO 01/29206, WO 00/28000, and WO 00/27995.

III.B. Phenotypes

Any detectable or measurable quality can be used to phenotype a cellular library of the presently claimed subject matter. Representative phenotypes that can be assessed in cultured cells include but are not limited to a visible phenotype (e.g., a morphological phenotype), a viability phenotype, a molecular phenotype, a differentiation phenotype, a cell behavioral phenotype, a susceptibility phenotype, a resistance phenotype, and combinations thereof, as described further herein below. These descriptive categories are not strictly defined and are also not mutually exclusive. Representative examples described herein below are exemplary and are not intended to limit the type of assay that can be performed.

Figure 5A:
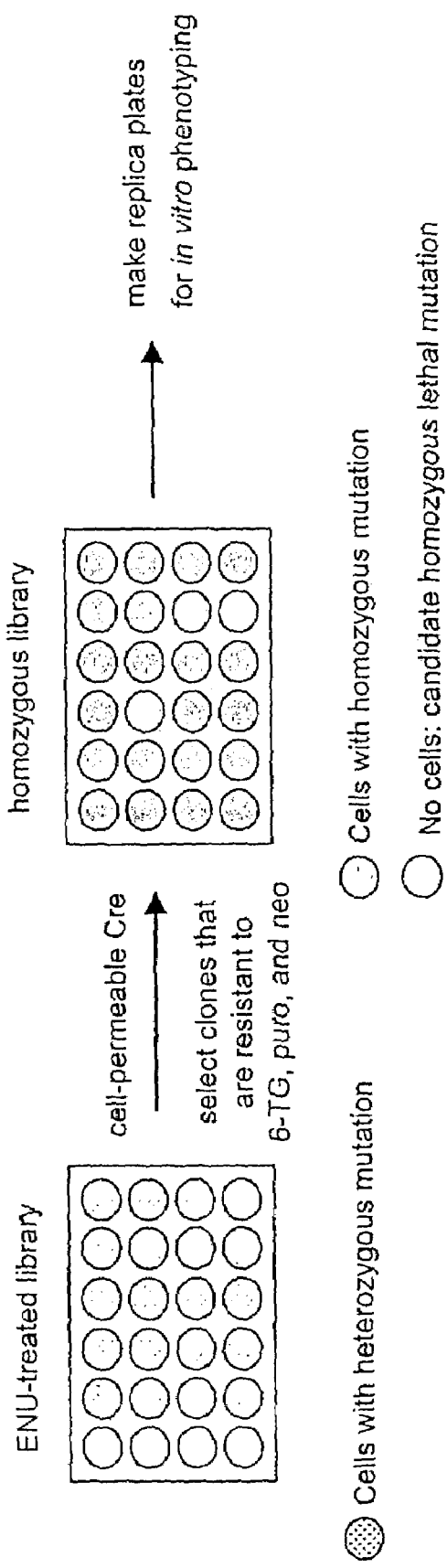
FIGS. 5A–5B are schematic drawings depicting preparation of a representative embodiment of a homozygous cellular library using the heterozygous cellular library of FIG. 4. See also Example 4.
Figure 5B:
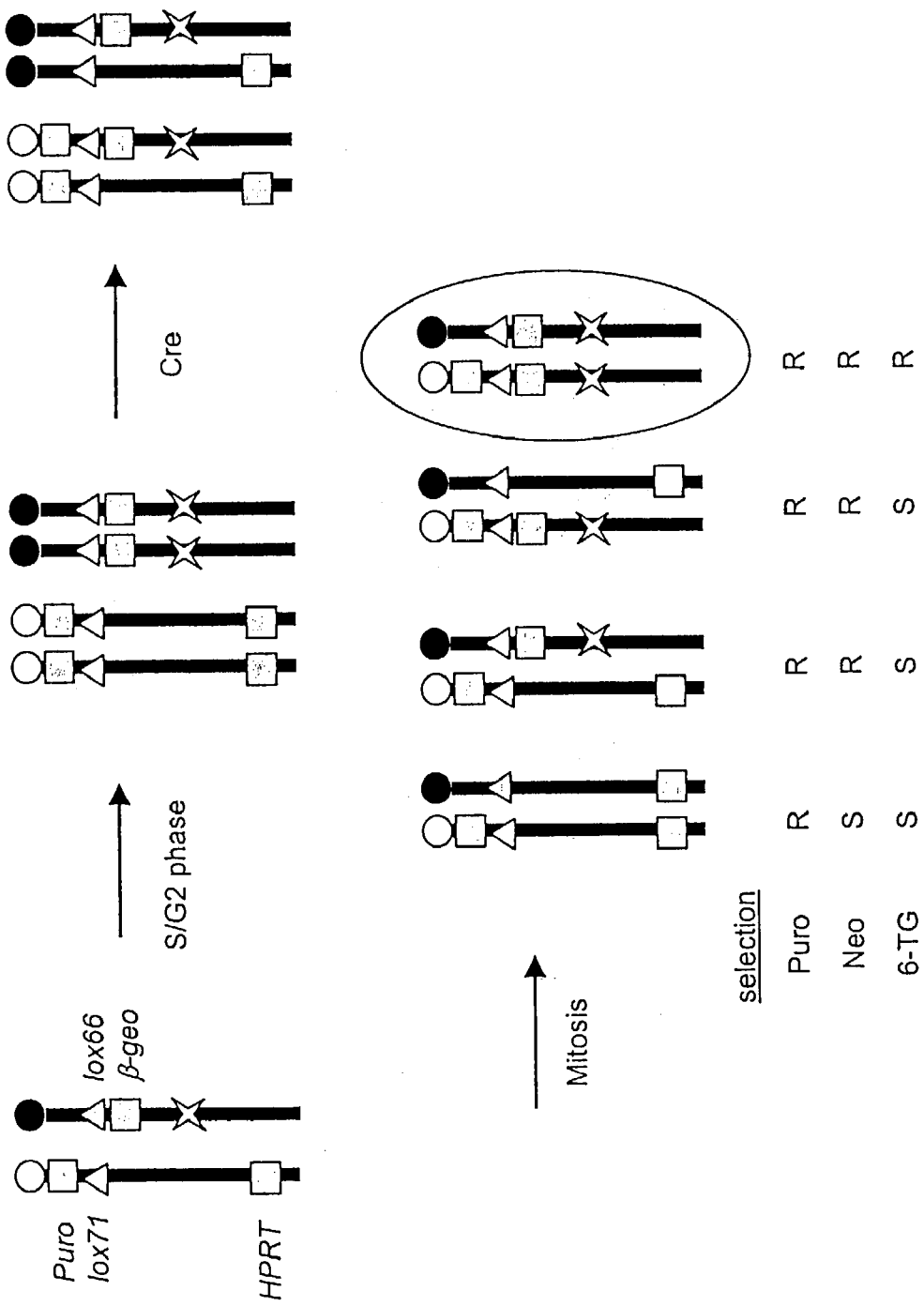

Cell Viability Phenotype. Any clone that is not recovered following induced mitotic recombination and selection comprises a candidate cell lethal mutation (FIG. 5A). Cell lethality can also be assayed in response to an environmental condition.

A cell lethal phenotype can be detected by observing a reduced number or absence of viable cells. Viability can be assessed, for example, by providing a substrate for mitochondrial dehydrogenase, wherein metabolism of the substrate by living cells can be detected calorimetrically. Other representative viability indicators include 3-(4,5-dimethylthiazole-2-yl)-2,5-diphenyl tetrazolium bromide (MTT), 2,3-Bis(2-methoxy-4-nitro-5-sulfophenyl)-2H-tetrazoium-5-carboxanilide (XTT) (available from Sigma, St. Louis, Mo., United States of America), and methylene blue. MTT and XTT are metabolized only in living cells to produce blue and orange formazan products, respectively. Methylene blue is decolorized by dehydrogenase activity of living cells. See U.S. Pat. No. 5,858,687.

Molecular Phenotypes. The term "molecular phenotype" refers to a detectable feature of molecules in a cell or organism. Representative molecular phenotypes include, but are not limited to a level of gene expression (e.g., a level of RNA or a level of protein), a protein modification, a protein activity (e.g., an enzyme activity), a level of lipid, production of a lipid type, a lipid modification, a level of carbohydrate, production of a carbohydrate type, a carbohydrate modification, and combinations thereof.

Methods for observing, detecting, and quantifying molecular phenotypes comprising altered levels of mRNA transcripts are well known to one skilled in the art. See Ausubel, 1995; Innis, 1990; Koduri & Poola, 2001.

Immunochemical approaches can be used to characterize a protein level or a protein structure. For example, techniques for detecting antibody-antigen conjugates or complexes include but are not limited to centrifugation, affinity chromatography and other immunochemical methods. See e.g., Manson, 1992; Ishikawa, 1999; Law, 1996; Chan, 1996; Liddell & Weeks, 1995; Masseyeff et al., 1993; Walker & Rapley, 1993; and references cited therein.

Additional methods for molecular analysis that can be used in a phenotyping assay of the presently claimed subject matter include high performance liquid chromatography (HPLC), capillary electrophoresis, and mass spectrometry, which can be adapted for high-throughput analyses.

The term "mass spectrometry" as used herein refers to techniques including but not limited to gas chromatography-mass spectrometry (GC-MS), liquid chromatography-mass spectrometry (LC-MS), laser-desorption mass spectrometry (LD-MS), matrix-assisted laser desorption/ionization mass spectrometry (MALDI-MS), time-of-flight mass spectrometry (TOF-MS), electrospray ionization mass spectrometry (ESI-MS); tandem mass spectroscopy, field release mass spectrometry, and combinations thereof. See e.g., Maurer, 2000; Karas et al., 2000; Kowalski & Stoerker, 2000; Griffiths et al., 2001; U.S. Pat. Nos. 6,107,623; 6,104,028; 6,093,300; 6,057,543; 6,017,693; 6,002,127; 5,118,937; 5,952,654; and references cited therein.

Determination of a molecular phenotype can also comprise a reagent-based assay, where a signal, for example a spectroscopic signal or a fluorescent signal, is measured in response to provision of a chromogenic or fluorogenic substrate. For example, chromogenic and fluorogenic substrates can be used to assay a variety of enzyme activities, including alcohol dehydrogenases, aldolases, lipases, amidases, epoxide hydrolases and phosphatases. See e.g., Wahler & Reymond, 2001, and references cited therein.

Common research equipment has been developed to perform high-throughput detection of spectroscopic and fluorescent signals, including instruments from GSI Lumonics (Watertown, Mass., United States of America), Amersham Pharmacia Biotech/Molecular Dynamics (Sunnyvale, Calif., United States of America), Applied Precision Inc. (Issauah, Wash., United States of America), and Genomic Solutions Inc. (Ann Arbor, Mich., United States of America).

Differentiation Phenotypes. The term "differentiation phenotype" generally refers to the ability of a precursor cell or a stem cell to generate one or more differentiated cell types. Particular cell types can be assessed, for example, by morphological inspection and/or determination of a molecular phenotype as described herein above.

Cell Behavioral Phenotypes. The term "cell behavioral phenotype" generally refers to cellular activities such as cell adhesion or attachment to a surface, cell aggregation, cell motility, cell division, cell growth, cell tropism or aversion, etc.

For example, a cell behavioral phenotype can comprise a frequency of beating activity in cardiomyocytes as described by Wobus et al., 2001.

A cell behavioral phenotype comprising a rate of cell growth can be measured, for example, by quantifying a cellular marker (e.g., an amount of antigen). See U.S. Pat. Nos. 5,912,132 and 5,707,798.

Cell division can be measured by quantification of bromodeoxyuridine incorporation or by Hoechst-ethidium bromide staining as described by Pollard & Walker, 1997.

Representative assays for measuring chemotaxis, for example chemotaxis to chemokines, are described in Proudfoot et al., 2000.

Physiological Phenotypes. The term "physiological phenotype" generally refers to the processes of ion conductance across a cell membrane. Representative measures of a physiological phenotype include, for example, a resting membrane potential, an amplitude or frequency of evoked potentials, ion permeability across a membrane, etc.

A physiological phenotype can be assayed using any technique known in the art, including extracellular single unit voltage recording, intracellular voltage recording, voltage clamping, and patch clamping. Representative methods for physiological analysis can be found, for example, in Sakmann & Neher, 1995; DeFelice, 1997; and U.S. Pat. No. 6,174,690.

A physiological phenotype can also be assayed by determining the flux of labeled tracer ions, for example as described by Catterall et al., 1981 and by Reith, 1990.

A variety of fluorescent molecules have been described that respond to changes in intracellular calcium concentration, membrane potential, and pH, and can also be used as indicators of receptor stimulation and ion channel activation. See e.g., Gonzales et al., 1999; Denyer et al., 1998; and references cited therein.

Specialized Cell Function Phenotypes. For cells with specialized functions, a phenotyping assay can also comprise a determination of a cellular activity. As one example, a phenotyping assay can be employed to determine a level of T cell activation or cytotoxicity as described by Kearse, 2000.

Susceptibility Phenotypes. The term "susceptibility phenotype" refers to an increased capacity or risk for displaying a phenotype, including but not limited to any phenotype noted herein above. For example, a susceptibility phenotype can comprise an increased frequency of cytotoxicity in the presence of a drug.

Resistance Phenotypes. Conversely, the term "resistance phenotype" refers to an increased capacity to resist expression of a phenotype including, but not limited to any phenotype noted herein above. For example, a resistance phenotype can comprise plant viability in the presence of an herbicide. As another example, a resistance phenotype can comprise reduced susceptibility to viral infection as described by Bedard et al., 1999.

IV. Mapping of Mutant Loci

The presently claimed subject matter further provides an in vitro method for mapping a genetic modification conferring a phenotype of interest. The method comprises: (a) culturing an isolated cell comprising one or more heterozygous genetic modifications (i.e., a random genetic variant), whereby a population of recombinant cells is produced; and (b) mapping the genomes of individuals within the population of recombinant cells that display a phenotype, whereby a genetic locus that modulates the phenotype is identified.

The term "recombinant cell" is used herein to refer to a cell that has undergone a random (non-induced) mitotic recombination event to make a chromosome that comprises heterozygous segments and homozygous segments.

Optionally, the method can further comprise selecting from among the population of recombinant genetic variants a subpopulation comprising a selectable marker, to thereby select cells comprising the genetic modification of interest.

As described herein above, a cell comprising a random genetic variant can be generated via random mutagenesis and typically comprises a heterozygous genetic modification. Thus, expansion of a cell derived from a heterozygous cellular library will produce a population of different cells as a result of mitotic recombination.

In one embodiment of the presently claimed subject matter, the culturing further comprises contacting the culture with an agent to promote mitotic recombination during expansion of the culture. Representative agents include inhibitors of DNA repair, such as a helicase inhibitor. For example, inhibitors of RecQ helicases, including porphyrin derivatives such as meso-tetra (N-methyl-4-pyridyl) porphine tetra tosylate (T4) and N-methyl mesoporphyrin IX (NMM), can be used to promote mitotic recombination as described in Example 6.

The terms "mapping" and "gene mapping" are used interchangeably to refer to progressive resolution of genomic sequence conferring a phenotype. A typical mapping experiment employs linkage analysis of a target locus and genetic polymorphisms. The results of a mapping method can be expressed as map units or centimorgans.

The term "polymorphism" refers to the occurrence of two or more genetically determined alternative sequences or alleles in a population. An allelic difference can be as small as one base pair.

The terms "Morgan" and "map unit" each refer to a unit for expressing a relative distance between genes on a chromosome. One Morgan unit (M) indicates a recombination frequency of 100%. A centimorgan (cM) indicates a recombination frequency of 1%. The term "recombination frequency" refers to a value calculated as a number of recombinants divided by the total number of progeny.

A mapping method employed in the methods of the presently claimed subject matter is selected to have sufficient power for resolution of a target locus. The term "power" as used herein refers to the probability of detecting or mapping a genetic locus. Power is in one embodiment 80%, in another embodiment 90%, in another embodiment 95%, and in still another embodiment 99%. The power of detection is correlated with target gene strength, and is optimal when genetic noise and environmental noise in the mapping population is low. Conversely, the power of detection is diminished by genetic noise and environmental noise.

The term "target gene" in the context of gene mapping refers to a gene that, when mutated, confers a phenotype of interest.

The term "strength" and "target gene strength" each refer to the percent contribution of a single gene to a phenotype. Gene strength correlates with ease of genetically detecting a target gene. Relatively strong target genes are easily detected. Genes with relatively weak effects contribute to complex traits, and are often masked by environmental noise.

The terms "genetic noise" and "genetic background" and "residual genotype" as used herein each refer to a level of genetic variation. In a gene mapping experiment, genetic noise is inversely correlated with genetic diversity. A level of genetic noise can be described by the equation:

$$\text{genetic noise} = \Sigma b_i x_i,$$

wherein b represents gene strength or allele substitution effect, x represents genotype, and i represents a number of non-target genes. Thus, genetic noise represents a sum of allele substitution effects at all non-target loci contributing to a phenotype. Optimally, the genetic noise should approach zero for maximum sensitivity of gene mapping.

The terms "environmental noise" and "environmental background" as used herein each refer to a level of environmental variation. In a gene mapping experiment, environmental noise is inversely correlated with experimental replication of identical genotypes. For example, environmental noise is significant when all individuals are unique. Optimally, environmental noise should approach zero for maximum sensitivity of gene mapping.

In accordance with the methods of the presently claimed subject matter, a mapping method can comprise an initial genome-wide scan using a population derived by expanding a cell comprising a random genetic variant. The progeny are genotyped to define an approximately 20 cM interval in which the target locus resides. A map location is then estimated using interval mapping or variations thereof, wherein linkage analysis is performed using additional genetic polymorphisms within the initially defined interval. Further evaluation of candidate genes within a small chromosomal interval is variably difficult depending on the resolution of the mapping and the power to detect genetic loci with small effects.

Techniques for gene mapping are well known to one skilled in the art, including linkage analysis (e.g., Wells & Brown, 2000), linkage disequilibrium analysis (Kruglyak, 1999), restriction landmark genomic scanning (RLGS) (Akiyoshi et al., 2000), and radiation hybrid mapping (Schuler et al., 1996; Van Etten et al., 1999). Any suitable mapping technique can be used, and it will be appreciated by one of skill in the art that no particular choice is essential to or a limitation of the presently claimed subject matter.

An exemplary method for gene mapping is linkage analysis whereby a phenotype is correlated with one or more detectable polymorphisms including but not limited to restriction fragment length polymorphisms (RFLPs) (Lander & Botstein, 1989), short tandem repeat polymorphisms (STRPs), short sequence length polymorphisms (SSLPs) (Dietrich et al., 1996), microsatellite markers (Schalkwyk et al., 1999), and single nucleotide polymorphisms (SNPs) (Brookes, 1999).

An exemplary technique for linkage analysis is detection of SNPs. The density of SNP markers in a mammalian genome is estimated to be about 1 SNP per 1 kb of sequence. See Collins et al, 1998. Several approaches can be used for typing SNPs, including homogenous hybridization assays (Livak et al., 1995), oligonucleotide ligation assays (Chen et al., 1998), matrix-assisted laser desorption time-of-flight mass spectrometry (MALDI-TOF) (Kwok, 1998; Ross et al., 1998), high performance liquid chromatography (HPLC) (Schriml et al., 2000), fluorescence polarization (Chen et al., 1999), array-based technologies (Cronin et al., 1996; Hacia et al., 1996; Pastinen et al., 1997; Gentalen & Chee, 1999; Sapolsky et al., 1999), pyrophosphate minisequencing (Nyren et al,1993), and invader methods (Griffin et al., 1999; Lyamichev et al., 1999). See also Landegren et al., 1998.

Exemplary methods for SNP detection are array-based oligonucleotide hybridization and minisequencing, described further herein below, as these techniques are amenable to high-throughput and multiplex formats. Oligonucleotide microarrays or chips can be manufactured by photolithographic synthesis of oligonucleotides onto glass slides using, for example, the AFFYMETRIX® system (Affymax Corporation of Greenford Middlesex, Great Britain) See Fodor et al., 1991 and U.S. Pat. No. 5,445,934. Alternatively, oligonucleotide microarrays can be produced by gridding oligonucleotides robotically onto the surface of a slide or other solid support (Schena et al., 1996), or by using an inkjet type technology to deliver oligonucleotides to a solid support (U.S. Pat. No. 5,965,352). By either method, a particular SNP is determined by a position of an oligonucleotide having an SNP in the array.

To detect a SNP using a hybridization assay, genomic fragments of a test genome are amplified by PCR and labeled such that the fragment is detectable. A SNP of the test genome is determined by the formation of a detectable heteroduplex structure at an identified position in the array.

To perform minisequencing reactions on chips, genomic fragments of a test genome are amplified using PCR and hybridized to an oligonucleotide microarray. Primer extension reactions including labeled nucleotides are performed on the hybridized oligonucleotide array. A SNP of the test genome is identified as a successful primer extension reaction assayed by detecting the labeled nucleotides. Alternatively, the SNP can be detected by amplification on the solid support without prior PCR.

To confirm mapping analyses, genomic clones within the mapped region, for example a BAC clone, can be transfected into mutagenized cells to thereby recover a wild type phenotype.

Regional cloning based on the genetic map position can be used to clone genes residing at the locus using methods known in the art. Alternatively, an integrated gene and physical map framework can be used to reference one or more genes at the mapping position, which can then be cloned using standard methods. See Klysik et al., 1999.

V. Assays of Gene Function in Whole Organisms

In one embodiment of the presently claimed subject matter, a cellular library comprises a plurality of ES cells, and a subset of ES cells are selected for further study following determination of an in vitro phenotype. To evaluate an organismal phenotype, a selected cell can be used to produce a genetic mosaic, a chimera, a cloned non-human organism, or combinations thereof. A plant cell that can be induced to form callus can be similarly used to generate plants for phenotypic analysis.

The term "genetic mosaic" refers to an organism comprising genetically related cells of more than one genotype. For example, a genetic mosaic organism can be generated by transplantation of mutagenized cells, or mutagenized and homozygosed cells, into a host organism from which they were originally derived.

The term "chimera" refers to an organism comprising cells from different sources. A genetic, mosaic organism can be produced using the regenerative methods described herein below.

The term "clone" is used herein to describe a regenerated organism, wherein all the cells of the organisms are genetically identical. Non-human animals can be cloned by nuclear transfer, as described herein below. Plants are readily regenerated using callus cells, also described herein below.

In one embodiment of the presently claimed subject matter, a chimeric animal can be generated by injection of ES cells into intact blastocysts or morula as described by Bradley et al., 1984. Representative protocols, markers for chimerism, and breeding strategies can be found in, for example, Papaionannou & Johnson, 2000.

A chimeric animal can also be generated by using ES cell aggregates as described by Nagy et al., 1990. Additional methods can be found in, for example, Bradley, 1987 and Nagy & Rossant, 2000.

In another embodiment of the presently claimed subject matter, cells of a cellular library, including stem cells, precursor cells, and differentiated cells, can be used to clone an animal via somatic nuclear transfer (Wilmut et al., 1997; Ashworth et al., 1998; Signer et al., 1998). Animals have been cloned from diverse differentiated cell types, including cells derived from mammary gland, cumulus, oviduct, granulosa, muscle, leukocyte, ear, skin, tail, and sertoli cells. Representative methods for somatic nuclear transfer can be found in, for example, Kato et al., 1998; Wells et al., 1999; Shiga et al., 1999; Zakhartchenko et al., 1999; Hill et al., 2000; Kubota et al., 2000; Wakayama et al., 1998; Wakayama & Yanagimachi, 1999; Ogura et al., 2000; Polejaeva et al., 2000.

Methods for plant regeneration are also known in the art and can be found, for example, in U.S. Pat. Nos. 6,091,004; 6,031,153; 5,986,082; and 5,792,904.

Mosaic, chimeric, and non-human cloned organisms can be studied to elucidate pathological phenotypes that are not readily detected at a cellular level including, but not limited to physiological, neurological, and organismal behavioral phenotypes. Any suitable method can be used to investigate phenotypes of mosaic, chimeric, and non-human cloned organisms, including in vivo as well as post-mortem analyses.

Representative techniques include external observation, magnetic resonance imaging (MRI), computerized tomography (CT), microscopy, and methods, histological methods, enzymatic assays, biochemical assays, assays to detect changes in gene transcription, including transcription profiling of multiple genes (e.g., chip analysis). In addition, in vitro phenotypic assays described herein above can be performed using cells derived from a mosaic, chimeric, or non-human cloned organism.

General approaches for pathological analysis are described in Agrios, 1997; Porth & Kunert, 2002, and references cited therein. Specific strategies and resources for analyzing mutant mice can be found in Bronson, 2001, and references cited therein.

EXAMPLES

The following Examples have been included to illustrate modes of the presently claimed subject matter. Certain aspects of the following Examples are described in terms of techniques and procedures found or contemplated by the present co-inventors to work well in the practice of the presently claimed subject matter. These Examples illustrate standard laboratory practices of the co-inventors. In light of the present disclosure and the general level of skill in the art, those of skill will appreciate that the following Examples are intended to be exemplary only and that numerous changes, modifications, and alterations can be employed without departing from the scope of the presently claimed subject matter.

Example 1

Preparation of ES Cells Comprising Marked Chromosomes

Non-recombinant inbred mouse strains C57BL/6J and 129S8/SvEv@J-Gpi1$^c$Hprt$^{b-m2}$ are crossed. ES cells are isolated from the resulting F1 progeny and maintained in an undifferentiated state by culturing them on a feeder cell layer.

Gene targeting methods were used to prepare ES cells comprising a pair of allelic recombination cassettes and a distal chromosome marker. A targeting vector p[Puro$^r$ lox71] was prepared comprising a [Puro$^r$ lox71] flanked by genomic sequences at the C57BL/6J D4Mit149 locus. A targeting vector p[lox66β-geo] was prepared comprising a [lox66β-geo] recombination cassette flanked by genomic sequences at the 129S8/SvEv@J-Gpil$^c$Hprt$^{b-m2}$ D4Mit149 locus. A targeting vector comprising a distal chromosome marker was prepared using an HPRT cDNA flanked by genomic sequence at the C57BL/6J D4Mit51 locus. The targeting vectors were sequentially electroporated into ES cells essentially as described by Stevens, 1983. Recombinants were selected by growth in media containing puromycin, neomycin, and hypoxanthine-aminopterin-thymidine (HAT).

Example 2

Preparation of a Heterozygous Cellular Library

ES cells comprising a marked chromosome pair are prepared as described in Example 1. Cells are grown in MEM culture medium supplemented with 15% heat-inactivated fetal calf serum, 1000 units/ml leukemia inhibitory factor (LIF), and 10 µM β-mercaptoethanol. Cells are grown on 100-mm petri dishes and cultured at 37° C. in a humidified atmosphere of 5% $CO_2$ in air. For subculturing, cells are dissociated in Hank's Balanced Salt Solution (HBSS) containing 0.25% trypsin and 0.02% ethylene diamine tetraacetic acid (EDTA). Following a 3-minute incubation at room temperature, dissociated cells are resuspended in culture medium, and the number of cells is determined using a hemocytometer. Culture media and supplements are available from Invitrogen Corp., Carlsbad, Calif., United States of America.

Plating efficiency is determined by determining the percentage of viable cells in mature cultures. Briefly, cells are plated at a density of about $2 \times 10^3$ cells per 100-mm petri dish, and the cells are cultured for about 6 days. The cells are then fixed in methanol and stained with 0.01% crystal violet. Viable cells are counted. Plating efficiency is expressed as a percentage of inoculated cells that are viable following culture. Culture conditions are modified as necessary to optimize plating efficiency.

Actively growing ES cells are trypsinized and plated at a density of about $5 \times 10^5$ cells per T25 flask. The cells are pre-incubated for 1 day and then treated with 0.3 mg/ml to 0.5 mg/ml ENU for about 5 hours. ENU stock solutions are prepared by dissolving ENU in medium without fetal calf serum. Vigorous shaking can be used to promote dissolution. ENU stock solutions are sterilized by passing through a 0.2 µm cellulose acetate filter immediately prior to use.

Surviving ES cells are subcultured at 3:1 onto 60-mm petri dishes in the presence of primary mouse embryonic fibroblasts (PMEFs). ES cells are cultured on PMEFs for about 2 days, and then subcultured at 3:1 onto 60-mm petri dishes without PMEFs. ES cells so-prepared are then cultured for about 5 days, trypsinized, and plated at a density of about $4 \times 10^5$ cells per 100-mm plate. The cells are cultured in the absence of PMEFs for about 6 days, at which time cells are individually plated in wells of a 96-well plate. The resulting plates of individual mutagenized ES cells comprise a heterozygous cellular library.

The library is cultured for a time sufficient to expand the library for the preparation of replica libraries. The replica libraries are alternately used for preparation of a homozygous cellular library (Example 4), for phenotypic screening (Example 5), and for gene mapping (Example 6). Replica libraries are cryopreserved as described in Example 3.

Example 3

Storage of Cellular Libraries

Cellular libraries and replica cellular libraries are preserved by storage in a cryopreservation medium at or below −70° C. Cryopreservation media generally consists of a base medium, a cryopreservative, and a protein source. The cryopreservative and protein protect the cells from the stress of the freeze-thaw process. For serum-containing medium, a typical cryopreservation medium is prepared as complete medium containing 10% glycerol; complete medium containing 10% DMSO (dimethylsulfoxide), or 50% cell-conditioned medium with 50% fresh medium with 10% glycerol or 10% DMSO. For serum-free medium, typical cryopreservation formulations include 50% cell-conditioned serum free medium with 50% fresh serum-free medium containing 7.5% DMSO; or fresh serum-free medium containing 7.5% DMSO and 10% cell culture grade DMSO. A cell suspension typically comprises about $10^6$ to about $10^7$ cells per ml is mixed with cryopreservation medium. Cellular libraries comprising ES cells can be frozen at a cellular density of about $5 \times 10^6$ cells/ml of freezing medium to about $10 \times 10^6$ cells/ml of freezing medium.

Cells can be cooled from room temperature to a storage temperature at a rate of about −1° C. per minute. The cooling rate is controlled, for example, by placing vials containing cells in an insulated water-filled reservoir having about 1 liter liquid capacity, and placing such cube in a −70° C. mechanical freezer. Alternatively, the rate of cell cooling is controlled at about −1° C. per minute by submersing vials in a volume of liquid refrigerant such as an aliphatic alcohol, the volume of liquid refrigerant being more than fifteen times the total volume of cell culture to be frozen, and placing the submersed culture vials in a conventional freezer at a temperature below about −70° C. Commercial devices for freezing cells are also available, for example, the Planer Mini-Freezer R202/200R (Planer Products Ltd., Great Britain) and the BF-5 Biological Freezer (Union Carbide Corporation, Danbury, Conn., United States of America). In one embodiment, frozen cells are stored at or below about −70° C. to about −80° C., and in another embodiment at or below about −130° C.

To obtain the best possible survival of the cells, thawing of the cells must be performed as quickly as possible. Once a vial or other reservoir containing frozen cells is removed from storage, it should be placed directly into a 37° C. water bath and gently shaken until it is completely thawed. If cells are particularly sensitive to cryopreservatives, the cells are centrifuged to remove cryopreservative prior to further growth.

Example 4

Preparation of a Homozygous Cellular Library

A cell-permeable Cre recombinase was prepared essentially as described by Jo et al., 2001. Briefly, a recombinant nucleic acid encoding a $His_6$-NLS-Cre-MTS polypeptide was expressed in *E. coli*, and the recombinant $His_6$-NLS- Cre-MTS polypeptide was purified by affinity chromatography, as directed by the supplier of the affinity matrix (Qiagen, Valencia, Calif., United States of America).

A cellular library of random genetic variants, or a replica thereof, is prepared as described in Example 2. The cellular library is cultured in serum-free medium containing about 10 μM His$_6$-NLS-Cre-MTS for about 2 hours. The cellular library is washed in serum-free medium for about 3 hours. The cellular library is then cultured in medium containing 10 μM 6-TG. Individual cells are re-plated such that the library format is maintained, and the cells are again cultured in medium containing 10 μM 6-TG. The resulting library comprises homozygous genetic variants. An identifiable position in the library (e.g., plate number and well number) of each random genetic variant and a homozygous genetic variant derived therefrom is preserved.

The cellular library of homozygous genetic variants is cultured for a time sufficient for the preparation of replica libraries. Replica libraries are prepared, which can then be employed in a variety of phenotypic screens (e.g., Example 5). Replica libraries cryopreserved as described in Example 3.

Example 5

Phenotypic Screening

Phenotypic screening is used to select cells comprising mutations that confer a phenotype of interest. A heterozygous cellular library, prepared as described in Example 2, is screened to identify dominant mutations. A homozygous cellular library, prepared as described in Example 3, is screened to identify recessive mutations.

Example 6

In Vitro Gene Mapping

A homozygous cellular library, prepared as described in Example 4, is screened to identify mutations conferring a phenotype of interest, as described in Example 5. Cells conferring the phenotype are identified according to a position in the library (e.g., plate number and well number). The corresponding cells from the heterozygous cellular library are identified and selected for mapping.

Each of the selected cells is cultured in medium containing meso-tetra (N-methyl-4-pyridyl) porphine tetra tosylate (T4) and N-methyl mesoporphyrin IX (NMM) (available from Porphyrin Products, Logan, Utah, United States of America). Conditions including porphyrin concentration and the duration of culture are empirically determined so as to optimize mitotic recombination, the number of recombinants recovered, and cellular viability. Cells of the expanded culture are washed in medium and then cultured in the presence of 10 μM 6-TG. Resistant cells are individually plated in 96-well plates, to thereby prepare a mapping population. The mapping population is used for mapping using recombination breakpoint delineation. In one embodiment, the mapping can localize the breakpoint to a 1 cM interval, and in another embodiment a 0.1 cM interval.

Once an interval has been defined, candidate genes within the region are tested for complementation. For example, a BAC clone comprising a candidate gene is introduced into a cell displaying a phenotype of interest, and rescue of the phenotype is scored. Alternatively or in addition, candidate genes are sequenced to identify genetic modifications.

REFERENCES

The publications and other materials listed below and/or set forth in the text above to illuminate the background of the presently claimed subject matter, and in particular cases, to provide additional details respecting the practice, are incorporated herein by reference. Materials used herein include, but are not limited to the following listed references.

Abbate J, Lacayo J C, Prichard M, Pari G & McVoy M A (2001) Bifunctional Protein Conferring Enhanced Green Fluorescence and Puromycin Resistance. *Biotechniques* 31:336–340.

Agrios G N (1997) *Plant Pathology*, 4th ed. Academic Press, San Diego, Calif., United States of America.

Akiyoshi S, Kanda H, Okazaki Y, Akama T, Nomura K, Hayashizaki Y & Kitagawa T (2000) A Genetic Linkage Map of the Msm Japanese Wild Mouse Strain with Restriction Landmark Genomic Scanning (RLGS). *Mamm Genome* 11:356–359.

Albert H, Dale E C, Lee E & Ow D W (1995) Site-Specific Integration of DNA into Wild-Type and Mutant Lox Sites Placed in the Plant Genome. *Plant J* 7:649–659.

Aoyama T & Chua N (1997) A Glucocorticoid-Mediated Transcriptional Induction System in Transgenic Plants. *The Plant Journal* 11:605–612.

Araki K, Araki M & Yamamura K (1997) Targeted Integration of DNA Using Mutant Lox Sites in Embryonic Stem Cells. *Nucleic Acids Res* 25:868–872.

Armaleo D, Ye G N, Klein T M, Shark K B, Sanford J C & Johnston S A (1990) Biolistic Nuclear Transformation of *Saccharomyces Cerevisiae* and Other Fungi. *Curr Genet* 17:97–103.

Ashworth D, Bishop M, Campbell K, Colman A, Kind A, Schnieke A, Blott S, Griffin H, Haley C, McWhir J & Wilmut I (1998) DNA Microsatellite Analysis of Dolly. *Nature* 394:329.

Ausubel F, ed (1995) *Short Protocols in Molecular Biology*, 3rd ed. Wiley, N.Y.

Bagutti C, Wobus A M, Fassler R & Watt F M (1996) Differentiation of Embryonal Stem Cells into Keratinocytes: Comparison of Wild-Type and Beta 1 Integrin-Deficient Cells. *Dev Biol* 179:184–196.

Bain G, Kitchens D, Yao M, Huettner J E & Gottlieb D I (1995) Embryonic Stem Cells Express Neuronal Properties in vitro. *Dev Biol* 168:342–357.

Bargmann C I (2001) High-Throughput Reverse Genetics: RNAi Screens in Caenorhabditis Elegans. Genome Biol 2.

Beckers J & Angelis MD (2002) Large-Scale Mutation Analysis for the Annotation of the Mouse Genome. *Curr Opin Chem Biol* 6:17–23.

Bedard J, May S, Barbeau D, Yuen L, Rando R F & Bowlin T L (1999) A High Throughput Colorimetric Cell Proliferation Assay for the Identification of Human Cytomegalovirus Inhibitors. *Antiviral Res* 41:35–43.

Bentley D J, Harrison C, Ketchen A M, Redhead N J, Samuel K, Waterfall M, Ansell J D & Melton D W (2002) DNA Ligase I Null Mouse Cells Show Normal DNA Repair Activity but Altered DNA Replication and Reduced Genome Stability. *J Cell Sci* 115:1551–1561.

Blochlinger K & Diggelmann H (1984) Hygromycin B Phosphotransferase as a Selectable Marker for DNA Transfer Experiments with Higher Eucaryotic Cells. *Mol Cell Biol* 4:2929–2931.

Bourouis M & Jarry B (1983) Vectors Containing a Prokaryotic Dihydrofolate Reductase Gene Transform Drosophila Cells to Methotrexate-Resistance. *Embo J* 2:1099–1104.

Bradley (1987) Production and Analysis of Cimaeric Mice. In: *Teratocarcinomas and Embryonic Stem Cells: A Practical Approach.* pp 113–151. IRL, Oxford/Wash., D.C.

Bradley A, Evans M, Kaufman M H & Robertson E (1984) Formation of Germ-Line Chimaeras from Embryo-Derived Teratocarcinoma Cell Lines. *Nature* 309:255–256.

Brenner S (1974) The Genetics of *Caenorhabditis Elegans*. *Genetics* 77:71–94.

Bronson R (2001) How to Study Pathological Phenotypes of Knockout Mice. In: *Gene Knockout Protocols.* pp 155–180. Humana Press, Totowa, N.J., United States of America.

Brookes A J (1999) The Essence of SNPs. *Gene* 234:177–186.

Buchholz F, Angrand P O & Stewart A F (1998) Improved Properties of FLP Recombinase Evolved by Cycling Mutagenesis. *Nat Biotechnol* 16:657–662.

Budziszewski G J, Lewis S P, Glover L W et al. (2001) *Arabidopsis Genes* Essential for Seedling Viability: Isolation of Insertional Mutants and Molecular Cloning. *Genetics* 159:1765–1778.

Caddick M X, Greenland A J, Jepson I, Krause K P, Qu N, Riddell K V, Salter M G, Schuch W, Sonnewald U & Tomselt A B (1998) An Ethanol Inducible Gene Switch for Plants Used to Manipulate Carbon Metabolism. *Nat Biotechnol* 16:177–180.

Capecchi M R (1980) High Efficiency Transformation by Direct Microinjection of DNA into Cultured Mammalian Cells. *Cell* 22:479–488.

Carthew R W (2001) Gene Silencing by Double-Stranded RNA. *Curr Opin Cell Biol* 13:244–248.

Catterall W A, Morrow C S, Daly J W & Brown G B (1981) Binding of Batrachotoxinin a 20-Alpha-Benzoate to a Receptor Site Associated with Sodium Channels in Synaptic Nerve Ending Particles. *J Biol Chem* 256:8922–8927.

Chatelin L, Volovitch M, Joliot A H, Perez F & Prochiantz A (1996) Transcription Factor Hoxa-5 Is Taken up by Cells in Culture and Conveyed to Their Nuclei. *Mech Dev* 55:111–117.

Chen X, Livak K J & Kwok P Y (1998) A Homogeneous, Ligase-Mediated DNA Diagnostic Test. *Genome Res* 8:549–556.

Chen X, Levine L & Kwok P Y (1999) Fluorescence Polarization in Homogeneous Nucleic Acid Analysis. *Genome Res* 9:492–498.

Chen Y T & Bradley A (2000) A New Positive/Negative Selectable Marker, Pudeltatk, for Use in Embryonic Stem Cells. *Genesis* 28:31–35.

Chibbar R, Kartha K, Daltla R & Leung N (1993) The Effect of Different Promoter-Sequences on Transient Expression of GUS Reporter Gene in Cultured Barley (Hordeum Vulgare L.) Cells. *Plant Cell Reports* 12:506.

Collins F S, Brooks L D & Chakravarti A (1998) A DNA Polymorphism Discovery Resource for Research on Human Genetic Variation. *Genome Res* 8:1229–1231.

Cronin M T, Fucini R V, Kim S M, Masino R S, Wespi R M & Miyada C G (1996) Cystic Fibrosis Mutation Detection by Hybridization to Light-Generated DNA Probe Arrays. *Hum Mutat* 7:244–255.

Dani C, Smith A G, Dessolin S, Leroy P, Staccini L, Villageois P, Darimont C & Ailhaud G (1997) Differentiation of Embryonic Stem Cells into Adipocytes in vitro. *J Cell Sci* 110:1279–1285.

DeFelice L J (1997) *Electrical Properties of Cells: Patch Clamp for Biologists.* Plenum Press, New York.

Denyer J, Worley J, Cox B, Allenby G & Banks M (1998) HTS Approaches to Voltage-Gated Ion Channel Drug Discovery. *Drug Discov Today* 3:323–332.

Derossi D, Chassaing G & Prochiantz A (1998) Trojan Peptides: The Penetratin System for Intracellular Delivery. *Trends Cell Biol* 8:84–87.

Dias J M, Go N F, Hart C P & Mattheakis L C (1998) Genetic Recombination as a Reporter for Screening Steroid Receptor Agonists and Antagonists. *Anal Biochem* 258:96–102.

Dietrich W F, Miller J, Steen R et al. (1996) A Comprehensive Genetic Map of the Mouse Genome. *Nature* 380:149–152.

Doetschman T, Williams P & Maeda N (1988) Establishment of Hamster Blastocyst-Derived Embryonic Stem (ES) Cells. *Dev Biol* 127:224–227.

Drab M, Haller H, Bychkov R, Erdmann B., Lindschau C, Haase H, Morano I, Luft F C & Wobus A M (1997) From Totipotent Embryonic Stem Cells to Spontaneously Contracting Smooth Muscle Cells: A Retinoic Acid and DB-cAMP in vitro Differentiation Model. *Faseb J* 11:905–915.

Driever W, Solnica-Krezel L, Schier A F, Neuhauss S C et al. (1996) A Genetic Screen for Mutations Affecting Embryogenesis in Zebrafish. *Development* 123:37–46.

Duffy J B, Harrison D A & Perrimon N (1998) Identifying Loci Required for Follicular Patterning Using Directed Mosaics. *Development* 125:2263–2271.

Eistetter H R (1988) A Mouse Pluripotent Embryonal Stem Cell Line Stage-Specifically Regulates Expression of Homeo-Box Containing DNA Sequences During Differentiation in vitro. *Eur J Cell Biol* 45:315–321.

Elliott G & O'Hare P (1997) Intercellular Trafficking and Protein Delivery by a Herpesvirus Structural Protein. *Cell* 88:223–233.

Esposito D & Scocca J J (1997) The Integrase Family of Tyrosine Recombinases: Evolution of a Conserved Active Site Domain. *Nucleic Acids Res* 25:3605–3614.

European Patent 1170354

Evans M J & Kaufman M H (1981) Establishment in Culture of Pluripotential Cells from Mouse Embryos. *Nature* 292:154–156.

Fahrer A M, Bazan J F, Papathanasiou P, Nelms K A & Goodnow C C (2001) A Genomic View of Immunology. *Nature* 409:836–838.

Fiering S, Kim C G, Epner E M & Groudine M (1993) An "in-out" Strategy Using Gene Targeting and FLP Recombinase for the Functional Dissection of Complex DNA Regulatory Elements: Analysis of the Beta-Globin Locus Control Region. *Proc Natl Acad Sci USA* 90:8469–8473.

Fodor S P, Read J L, Pirrung M C, Stryer L, Lu A T & Solas D (1991) Light-Directed, Spatially Addressable Parallel Chemical Synthesis. *Science* 251:767–773.

Fraichard A, Chassande O, Bilbaut A, Dehay C, Savatier P & Samarut J (1995) In Vitro Differentiation of Embryonic Stem Cells into Glial Cells and Functional Neurons. *J Cell Sci* 108:3181–3188.

Frankel A D & Pabo C O (1988) Cellular Uptake of the TAT Protein from Human Immunodeficiency Virus. *Cell* 55:1189–1193.

Freshney R I (1987) *Culture of Animal Cells: A Manual of Basic Technique,* 2nd ed. A. R. Liss, New York.

Friedrich G & Soriano P (1991) Promoter Traps in Embryonic Stem Cells: A Genetic Screen to Identify and Mutate Developmental Genes in Mice. *Genes Dev* 5:1513–1523.

Gans M, Audit C & Masson M (1975) Isolation and Characterization of Sex-Linked Female-Sterile Mutants in *Drosophila Melanogaster*. *Genetics* 81:683–704.

Gentalen E & Chee M (1999) A Novel Method for Determining Linkage between DNA Sequences: Hybridization to Paired Probe Arrays. *Nucleic Acids Res* 27:1485–1491.

Glover D M & Hames B D (1995) *DNA Cloning: A Practical Approach*, 2nd ed. IRL Press at Oxford University Press, Oxford/N.Y.

Gonzales J, Oades K, Leychkis Y, Harootunian A & Negulescu P (1999) Cell Based Assays and Instrumentation for Screening Ion-Channel Targets. *Drug Discov Today* 4:431–439.

Grainge I & Jayaram M (1999) The Integrase Family of Recombinase: Organization and Function of the Active Site. *Mol Microbiol* 33:449–456.

Green M & Loewenstein P M (1988) Autonomous Functional Domains of Chemically Synthesized Human Immunodeficiency Virus TAT Trans-Activator Protein. *Cell* 55:1179–1188.

Griffin T J, Hall J G, Prudent J R & Smith L M (1999) Direct Genetic Analysis by Matrix-Assisted Laser Desorption/Ionization Mass Spectrometry. *Proc Natl Acad Sci USA* 96:6301–6306.

Griffiths W J, Jonsson A P, Liu S, Rai D K & Wang Y (2001) Electrospray and Tandem Mass Spectrometry in Biochemistry. *Biochem J* 355:545–561.

Groth A C, Olivares E C, Thyagarajan B & Calos M P (2000) A Phage Integrase Directs Efficient Site-Specific Integration in Human Cells. *Proc Natl Acad Sci USA* 97:5995–6000.

Hacia J G, Brody L C, Chee M S, Fodor S P & Collins F S (1996) Detection of Heterozygous Mutations in BRCA1 Using High Density Oligonucleotide Arrays and Two-Colour Fluorescence Analysis. *Nat Genet* 14:441–447.

Haffter P, Granato M, Brand M et al. (1996) The Identification of Genes with Unique and Essential Functions in the Development of the Zebrafish, Danio Rerio. *Development* 123:1–36.

Hanin M, Volrath S, Bogucki A, Briker M, Ward E & Paszkowski J (2001.) Gene Targeting in *Arabidopsis*. *Plant J* 28:671–677.

Hanks M, Wurst W, Anson-Cartwright L, Auerbach A B & Joyner A L (1995) Rescue of the EN-1 Mutant Phenotype by Replacement of EN-1 with EN-2. *Science* 269:679–682.

Hanson K D & Sedivy J M (1995) Analysis of Biological Selections for High-Efficiency Gene Targeting. *Mol Cell Biol* 15:45–51.

Hasty P, Abuin A & Bradley A (2000) Gene Targeting, Principles, and Practice in Mammalian Cells. In: *Gene Targeting: A Practical Approach*, 2nd ed. pp 1–36. Oxford University Press, Oxford.

Hattori M, Fujiyama A, Taylor T D et al. (2000) The DNA Sequence of Human Chromosome 21. *Nature* 405:311–319.

He J & Furmanski P (1995) Sequence Specificity and Transcriptional Activation in the Binding of Lactoferrin to DNA. *Nature* 373:721–724.

Herault Y, Rassoulzadegan M, Cuzin F & Duboule D (1998) Engineering Chromosomes in Mice through Targeted Meiotic Recombination (TAMERE). *Nat Genet* 20:381–384.

Hill J R, Burghardt R C, Jones K, Long C R, Looney C R, Shin T, Spencer T E, Thompson J A, Winger Q A & Westhusin M E (2000) Evidence for Placental Abnormality as the Major Cause of Mortality in First-Trimester Somatic Cell Cloned Bovine Fetuses. *Biol Reprod* 63:1787–1794.

Hoess R H, Ziese M & Sternberg N (1982) P1 Site-Specific Recombination: Nucleotide Sequence of the Recombining Sites. *Proc Natl Acad Sci USA* 79:3398–3402.

Hole N & Smith A (1994) Embryonic Stem Cells and Hematopoiesis. In: *Culture of Hematopoietic Cells*. pp 235–249. Wiley-Liss, New York.

Hrabe de Angelis M H, Flaswinkel H, Fuchs H et al. (2000) Genome-Wide, Large-Scale Production of Mutant Mice by ENU Mutagenesis. *Nat Genet* 25:444–447.

Isaacs A M, Davies K E, Hunter A J et al. (2000) Identification of Two New Pmp22 Mouse Mutants Using Large-Scale Mutagenesis and a Novel Rapid Mapping Strategy. *Hum Mol Genet* 9:1865–1871.

Jayaram M (1985) Two-Micrometer Circle Site-Specific Recombination: The Minimal Substrate and the Possible Role of Flanking Sequences. *Proc Natl Acad Sci USA* 82:5875–5879.

Jo D, Nashabi A, Doxsee C, Lin Q, Unutmaz D, Chen J & Ruley H E (2001) Epigenetic Regulation of Gene Structure and Function with a Cell-Permeable Cre Recombinase. *Nat Biotechnol* 19:929–933.

Joliot A, Pernelle C, Deagostini-Bazin H & Prochiantz A (1991) Antennapedia Homeobox Peptide Regulates Neural Morphogenesis. *Proc Natl Acad Sci USA* 88:1864–1868.

Joliot A, Maizel A, Rosenberg D, Trembleau A, Dupas S, Volovitch M & Prochiantz A (1998) Identification of a Signal Sequence Necessary for the Unconventional Secretion of Engrailed Homeoprotein. *Curr Biol* 8:856–863.

Joyner A L (2000) *Gene Targeting: A Practical Approach*, 2nd ed. Oxford University Press, Oxford.

Kanegae Y, Lee G, Sato Y, Tanaka M, Nakai M, Sakaki T, Sugano S & Saito I (1995) Efficient Gene Activation in Mammalian Cells by Using Recombinant Adenovirus Expressing Site-Specific Cre Recombinase. *Nucleic Acids Res* 23:3816–3821.

Karas M, Bahr U & Dulcks T (2000) Nano-Electrospray Ionization Mass Spectrometry: Addressing Analytical Problems Beyond Routine. *Fresenius J Anal Chem* 366:669–676.

Karin M, Haslinger A, Holtgreve H, Cathala G, Slater E & Baxter J D (1984) Activation of a Heterologous Promoter in Response to Dexamethasone and Cadmium by Metallothionein Gene 5'-Flanking DNA. *Cell* 36:371–379.

Kasarskis A, Manova K & Anderson K V (1998) A Phenotype-Based Screen for Embryonic Lethal Mutations in the Mouse. *Proc Natl Acad Sci USA* 95:7485–7490.

Kato Y, Tani T, Sotomaru Y, Kurokawa K, Kato J, Doguchi H, Yasue H & Tsunoda Y (1998) Eight Calves Cloned from Somatic Cells of a Single Adult. *Science* 282:2095–2098.

Kearse K P (2000) *T Cell Protocols: Development and Activation*. Humana Press, Totowa, N.J., United States of America.

Keller G M (1995) In Vitro Differentiation of Embryonic Stem Cells. *Curr Opin Cell Biol* 7:862–869.

Kemphues K J, Priess J R, Morton D G & Cheng N S (1988) Identification of Genes Required for Cytoplasmic Localization in Early *C. Elegans* Embryos. *Cell* 52:311–320.

Kempin S A, Liljegren S J, Block L M, Rounsley S D, Yanofsky M F & Lam E (1997) Targeted Disruption in *Arabidopsis*. *Nature* 389:802–803.

Keresztes M & Boonstra J (1999) Import(Ance) of Growth Factors in(to) the Nucleus. *J Cell Biol* 145:421–424.

Khrebtukova I, Michaud E J, Foster C M, Stark K L, Garfinkel D J & Woychik R P (1998) Utilization of Microhomologous Recombination in Yeast to Generate Targeting Constructs for Mammalian Genes. *Mutat Res* 401:11–25.

Klysik J, Cai W W, Yang C & Bradley A (1999) An Integrated Gene and SSLP BAC Map Framework of Mouse Chromosome 11. *Genomics* 62:123–128.

Koduri S & Poola I (2001) Quantitation of Alternatively Spliced Estrogen Receptor Alpha mRNAs as Separate Gene Populations. *Steroids* 66:17–23.

Kolb A & Neumann K (1997) Beyond the 96-Well Microplate: Instruments and Assay Methods for the 384-Well Format. *J Biomol Screen* 2:103–109.

Kolot M, Silberstein N & Yagil E (1999) Site-Specific Recombination in Mammalian Cells Expressing the Int Recombinase of Bacteriophage HK022. *Mol Biol Rep* 26:207–213.

Koresawa Y, Miyagawa S, Ikawa M, Matsunami K, Yamada M, Shirakura R & Okabe M (2000) Synthesis of a New Cre Recombinase Gene Based on Optimal Codon Usage for Mammalian Systems. *J Biochem (Tokyo)* 127:367–372.

Kowalski P & Stoerker J (2000) Accelerating Discoveries in the Proteome and Genome with MALDI TOF MS. *Pharmacogenomics* 1:359–366.

Kruglyak L (1999) Prospects for Whole-Genome Linkage Disequilibrium Mapping of Common Disease Genes. *Nat Genet* 22:139–144.

Kubota C, Yamakuchi H, Todoroki J, Mizoshita K, Tabara N, Barber M & Yang X (2000) Six Cloned Calves Produced from Adult Fibroblast Cells after Long-Term Culture. *Proc Natl Acad Sci USA* 97:990–995.

Kwok P Y (1998) Genotyping by Mass Spectrometry Takes Flight. *Nat Biotechnol* 16:1314–1315.

Landegren U, Kaiser R, Caskey C T & Hood L (1988) DNA Diagnostics—Molecular Techniques and Automation. *Science* 242:229–237.

Lander E S & Botstein D (1989) Mapping Mendelian Factors Underlying Quantitative Traits Using RFLP Linkage Maps. *Genetics* 121:185–199.

Lander E S, Linton L M, Birren B et al. (2001) Initial Sequencing and Analysis of the Human Genome. *Nature* 409:860–921.

Landy A (1989) Dynamic, Structural, and Regulatory Aspects of Lambda Site-Specific Recombination. *Annu Rev Biochem* 58:913–949.

Landy A (1993) Mechanistic and Structural Complexity in the Site-Specific Recombination Pathways of Int and FLP. *Curr Opin Genet Dev* 3:699–707.

Lebel E, Heifetz P, Thorne L, Uknes S, Ryals J & Ward E (1998) Functional Analysis of Regulatory Sequences Controlling PR-1 Gene Expression in *Arabidopsis*. *The Plant Journal* 16:223–233.

Lebel M & Leder P (1998) A Deletion within the Murine Werner Syndrome Helicase Induces Sensitivity to Inhibitors of Topoisomerase and Loss of Cellular Proliferative Capacity. *Proc Natl Acad Sci USA* 95:13097–13102.

Lee G & Saito I (1998) Role of Nucleotide Sequences of LoxP Spacer Region in Cre-Mediated Recombination. *Gene* 216:55–65.

Lin Y Z, Yao S Y, Veach R A, Torgerson T R & Hawiger J (1995) Inhibition of Nuclear Translocation of Transcription Factor Nf-Kappa B by a Synthetic Peptide Containing a Cell Membrane-Permeable Motif and Nuclear Localization Sequence. *J Biol Chem* 270:14255–14258.

Lindgren M, Hallbrink M, Prochiantz A & Langel U (2000) Cell-Penetrating Peptides. *Trends Pharmacol Sci* 21:99–103.

Liu P, Jenkins N A & Copeland N G (2002) Efficient Cre-Loxp-Induced Mitotic Recombination in Mouse Embryonic Stem Cells. *Nat Genet* 30:66–72.

Livak K J, Marmaro J & Todd J A (1995) Towards Fully Automated Genome-Wide Polymorphism Screening. *Nat Genet* 9:341–342.

Lyamichev V, Mast A L, Hall J G et al. (1999) Polymorphism Identification and Quantitative Detection of Genomic DNA by Invasive Cleavage of Oligonucleotide Probes. *Nat Biotechnol* 17:292–296.

Maeser S & Kahmann R (1991) The Gin Recombinase of Phage Mu Can Catalyse Site-Specific Recombination in Plant Protoplasts. *Mol Gen Genet* 230:170–176.

Maffia A M, 3rd, Kariv II & Oldenburg K R (1999) Miniaturization of a Mammalian Cell-Based Assay: Luciferase Reporter Gene Readout in a 3 Microliter 1536-Well Plate. *J Biomol Screen* 4:137–142.

Magnuson T, Epstein C J, Silver L M & Martin G R (1982) Pluripotent Embryonic Stem Cell Lines Can Be Derived from Tw5/Tw5 Blastocysts. *Nature* 298:750–753.

Maltsev V A, Rohwedel J, Hescheler J & Wobus A M (1993) Embryonic Stem Cells Differentiate in vitro into Cardiomyocytes Representing Sinusnodal, Atrial and Ventricular Cell Types. *Mech Dev* 44:41–50.

Maltsev V A, Wobus A M, Rohwedel J, Bader M & Hescheler J (1994) Cardiomyocytes Differentiated in vitro from Embryonic Stem Cells Developmentally Express Cardiac-Specific Genes and Ionic Currents. *Circ Res* 75:233–244.

Mannino R J & Gould-Fogerite S (1988) Liposome Mediated Gene Transfer. *Biotechniques* 6:682–690.

Marker P C, Seung K, Bland A E, Russell L B & Kingsley D M (1997) Spectrum of Bmp5 Mutations from Germline Mutagenesis Experiments in Mice. *Genetics* 145:435–443.

Martin G R (1981) Isolation of a Pluripotent Cell Line from Early Mouse Embryos Cultured in Medium Conditioned by Teratocarcinoma Stem Cells. *Proc Natl Acad Sci USA* 78:7634–7638.

Matsui Y, Zsebo K & Hogan B L (1992) Derivation of Pluripotential Embryonic Stem Cells from Murine Primordial Germ Cells in Culture. *Cell* 70:841–847.

Maurer H H (2000) Screening Procedures for Simultaneous Detection of Several Drug Classes Used for High Throughput Toxicological Analyses and Doping Control. A Review. *Comb Chem High Throughput Screen* 3:467–480.

McCreath K J, Howcroft J, Campbell K H, Colman A, Schnieke A E & Kind A J (2000) Production of Gene-Targeted Sheep by Nuclear Transfer from Cultured Somatic Cells. *Nature* 405:1066–1069.

McElroy D, Zhang W, Cao J & Wu R (1990) Isolation of an Efficient Actin Promoter for Use in Rice Transformation. *Plant Cell* 2:163–172.

McElroy D, Blowers A, Jenes B & Wu R (1991) Construction of Expression Vectors Based on the Rice Actin 1 (Act1) 5' Region for Use in Monocot Transformation. *Molecular and General Genetics* 231:150–160.

McElver J, Tzafrir I, Aux G et al. (2001) Insertional Mutagenesis of Genes Required for Seed Development in *Arabidopsis Thaliana*. *Genetics* 159:1751–1763

McLeod M, Craft S & Broach J R (1986) Identification of the Crossover Site During FLP-Mediated Recombination in the Saccharomyces Cerevisiae Plasmid 2 Microns Circle. *Mol Cell Biol* 6:3357–3367.

McPherson J D, Marra M, Hillier L et al. (2001) A Physical Map of the Human Genome. *Nature* 409:934–941.

Mere L, Bennett T, Coassin P, England P, Hamman B, Rink T, Zimmerman S & Negulescu P (1999) Miniaturized FRET Assays and Microfluidics: Key Components for Ultra-High-Throughput Screening. *Drug Discov Today* 4:363–369.

Miller-Hance W C, LaCorbiere M, Fuller S J, Evans S M, Lyons G, Schmidt C, Robbins J & Chien K R (1993) In Vitro Chamber Specification During Embryonic Stem Cell Cardiogenesis. Expression of the Ventricular Myosin Light Chain-2 Gene Is Independent of Heart Tube Formation. *J Biol Chem* 268:25244–25252.

Nagy A (2000) Cre Recombinase: The Universal Reagent for Genome Tailoring. *Genesis* 26:99–109.

Nagy A & Rossant J (2000) Production and Analysis of ES Cell Aggregation Chimeras. In: *Gene Targeting: A Practical Approach,* 2nd ed. pp 177–206. Oxford University Press, Oxford.

Nagy A, Gocza E, Diaz E M, Prideaux V R, Ivanyi E, Markkula M & Rossant J (1990) Embryonic Stem Cells Alone Are Able to Support Fetal Development in the Mouse. *Development* 110:815–821.

Nolan P M, Peters J, Strivens M et al. (2000) A Systematic, Genome-Wide, Phenotype-Driven Mutagenesis Programme for Gene Function Studies in the Mouse. *Nat Genet* 25:440–443.

Norris S, Meyer S & Callis J (1993) The Intron of *Arabidopsis Thaliana Polyubiquitin* Genes Is Conserved in Location and Is a Quantitative Determinant of Chimeric Gene Expression. *Plant Molecular Biology* 21:895–906.

Nusslein-Volhard C & Wieschaus E (1980) Mutations Affecting Segment Number and Polarity in Drosophila. *Nature* 287:795–801.

Nyren P, Pettersson B & Uhlen M (1993) Solid Phase DNA Minisequencing by an Enzymatic Luminometric Inorganic Pyrophosphate Detection Assay. *Anal Biochem* 208: 171–175.

Oehlke J, Scheller A, Wiesner B, Krause E, Beyermann M, Klauschenz E, Meizig M & Bienert M (1998) Cellular Uptake of an Alpha-Helical Amphipathic Model Peptide with the Potential to Deliver Polar Compounds into the Cell Interior Non-Endocytically. *Biochim Biophys Acta* 1414:127–139.

Offringa R & Hooykaas P (1995) Gene Targeting in Plants. In: *Gene Tarqeting.* pp 83–122. CRC Press, Boca Raton, Fla., United States of America.

Ogura A, Inoue K, Ogonuki N, Noguchi A, Takano K, Nagano R, Suzuki O, Lee J, Ishino F & Matsuda J (2000) Production of Male Cloned Mice from Fresh, Cultured, and Cryopreserved Immature Sertoli Cells. *Biol Reprod* 62:1579–1584.

Oh S C, Nam S Y, Kwon H C, Kim C M, Seo J S, Seong R H, Jang Y J, Chung Y H & Chung H Y (2001) Generation of Fusion Genes Carrying Drug Resistance, Green Fluorescent Protein, and Herpes Simplex Virus Thymidine Kinase Genes in a Single Cistron. *Mol Cells* 11:192–197.

Okabe S, Forsberg-Nilsson K, Spiro A C, Segal M & McKay R D (1996) Development of Neuronal Precursor Cells and Functional Postmitotic Neurons from Embryonic Stem Cells in vitro. *Mech Dev* 59:89–102.

Olivares E C, Hollis R P & Calos M P (2001) Phage R4 Integrase Mediates Site-Specific Integration in Human Cells. *Gene* 278:167–176.

Oram M, Szczelkun M D & Halford S E (1995) Recombination. Pieces of the Site-Specific Recombination Puzzle. *Curr Biol* 5:1106–1109.

Papaionannou V & Johnson R (2000) Production of Chimeras by Blastocyst and Morula Injection of Targeted ES Cells. In: *Gene Targeting: A Practical Approach,* 2nd ed. pp 133–176. Oxford University Press, Oxford.

Parinov S & Sundaresan V (2000) Functional Genomics in *Arabidopsis*: Large-Scale Insertional Mutagenesis Complements the Genome Sequencing Project. *Curr Opin Biotechnol* 11:157–161.

Pastinen T, Kurg A, Metspalu A, Peltonen L & Syvanen A C (1997) Minisequencing: A Specific Tool for DNA Analysis and Diagnostics on Oligonucleotide Arrays. *Genome Res* 7:606–614.

PCT International Publication No. WO 01/11019
PCT International Publication No. WO 01/23545
PCT International Publication No. WO 01/29206
PCT International Publication No. WO 02/04609
PCT International Publication No. WO 00/27995
PCT International Publication No. WO 00/28000
PCT International Publication No. WO 95/06723
PCT International Publication No. WO 97/20035
PCT International Publication No. WO 99/25851
PCT International Publication No. WO 99/67361

Pellegrini O, Davenas E, Morin L, Tsangaris G T, Benveniste J, Manuel Y & Thomas Y (1994) Modulation of Stress Proteins by CD2+ in a Human T Cell Line. *Eur J Pharmacol* 270:221–228.

Polejaeva I A, Chen S H, Vaught T D, Page R L, Mullins J, Ball S, Dai Y, Boone J, Walker S, Ayares D L, Colman A & Campbell K H (2000) Cloned Pigs Produced by Nuclear Transfer from Adult Somatic Cells. *Nature* 407: 86–90.

Pollard J W & Walker J M (1997) *Basic Cell Culture Protocols,* 2nd ed. Humana Press, Totowa, N.J., United States of America.

Pooga M, Hallbrink M, Zorko M & Langel U (1998a) Cell Penetration by Transportan. *Faseb J* 12:67–77.

Pooga M, Lindgren M, Hallbrink M, Brakenhielm E & Langel U (1998b) Galanin-Based Peptides, Galparan and Transportan, with Receptor-Dependent and Independent Activities. *Ann NY Acad Sci* 863:450–453.

Porth C & Kunert M P (2002) *Pathophysiology: Concepts of Altered Health States,* 6th ed. Lippincott Williams & Wilkins, Philadelphia, Pa., United States of America.

Potter H, Weir L & Leder P (1984) Enhancer-Dependent Expression of Human Kappa Immunoglobulin Genes Introduced into Mouse Pre-βLymphocytes by Electroporation. *Proc Natl Acad Sci USA* 81:7161–7165.

Prochiantz A (2000) Messenger Proteins: Homeoproteins, TAT and Others. *Curr Opin Cell Biol* 12:400–406.

Proudfoot A E I, Wells T N C & Power C (2000) *Chemokine Protocols.* Humana Press, Totowa, N.J., United States of America.

Rassoulzadegan M, Binetruy B & Cuzin F (1982) High Frequency of Gene Transfer after Fusion between Bacteria and Eukaryotic Cells. *Nature* 295:257–259.

Reid L H, Gregg R G, Smithies O & Koller B H (1990) Regulatory Elements in the Introns of the Human Hprt Gene Are Necessary for Its Expression in Embryonic Stem Cells. *Proc Natl Acad Sci USA* 87:4299–4303.

Reith M E (1990) [14C]Guanidinium Ion Influx into Na+ Channel Preparations from Mouse Cerebral Cortex. *Eur J Pharmacol* 188:33–41.

Resnick J L, Bixler L S, Cheng L & Donovan P J (1992) Long-Term Proliferation of Mouse Primordial Germ Cells in Culture. *Nature* 359:550–551.

Rinaldi A, Marshall K R & Preston C M (1999) A Non-Cytotoxic Herpes Simplex Virus Vector Which Expresses Cre Recombinase Directs Efficient Site Specific Recombination. *Virus Res* 65:11–20.

Rinchik E M (1991) Chemical Mutagenesis and Fine-Structure Functional Analysis of the Mouse Genome. *Trends Genet* 7:15–21.

Risau W, Sariola H, Zerwes H G, Sasse J, Ekblom P, Kemler R & Doetschman T (1988) Vasculogenesis and Angiogenesis in Embryonic-Stem-Cell-Derived Embryoid Bodies. *Development* 102:471–478.

Risseeuw E, Offringa R, Franke-van Dijk M E & Hooykaas P J (1995) Targeted Recombination in Plants Using Agrobacterium Coincides with Additional Rearrangements at the Target Locus. *Plant J* 7:109–119.

Rohwedel J, Maltsev V, Bober E, Arnold H H, Hescheler J & Wobus A M (1994) Muscle Cell Differentiation of Embryonic Stem Cells Reflects Myogenesis in vivo: Developmentally Regulated Expression of Myogenic Determination Genes and Functional Expression of Ionic Currents. *Dev Biol* 164:87–101.

Rose O, Rohwedel J, Reinhardt S, Bachmann M, Cramer M, Rotter M, Wobus A & Starzinski-Powitz A (1994) Expression of M-Cadherin Protein in Myogenic Cells During Prenatal Mouse Development and Differentiation of Embryonic Stem Cells in Culture. *Dev Dyn* 201:245–259.

Ross P, Hall L, Smirnov I & Haff L (1998) High Level Multiplex Genotyping by MALDI-TOF Mass Spectrometry. *Nat Biotechnol* 16:1347–1351.

Rossant J & McKerlie C (2001) Mouse-Based Phenogenomics for Modelling Human Disease. *Trends Mol Med* 7:502–507.

Russell (1990) Factors Affecting the Nature of Induced Mutations. In: *Biology of Mammalian Germ-Cell Mutagenesis. Banbury Report* 34. pp 271–289. Cold Spring Harbor Laboratory Press, Cold Spring Harbor, N.Y.

Sachidanandam R, Weissman D, Schmidt S C et al. (2001) A Map of Human Genome Sequence Variation Containing 1.42 Million Single Nucleotide Polymorphisms. *Nature* 409:928–933.

Sadowski P D (1995) The FLP Recombinase of the 2-Microns Plasmid of Saccharomyces Cerevisiae. *Prog Nucleic Acid Res Mol Biol* 51:53–91.

Sakmann B & Neher E (1995) *Single-Channel Recording,* 2nd ed. Plenum Press, New York.

Sambrook et al. e (1989) *Molecular Cloning: A Laboratory Manual.* Cold Spring Harbor Laboratory Press, Cold Spring Harbor, N.Y.

Sapolsky R J, Hsie L, Berno A, Ghandour G, Mittmann M & Fan J B (1999) High-Throughput Polymorphism Screening and Genotyping with High-Density Oligonucleotide Arrays. *Genet Anal* 14:187–192.

Sauer B & Henderson N (1988) Site-Specific DNA Recombination in Mammalian Cells by the Cre Recombinase of Bacteriophage P1. *Proc Natl Acad Sci USA* 85:5166–5170.

Schaft J, Ashery-Padan R, van der Hoeven F, Gruss P & Stewart A F (2001) Efficient Flp Recombination in Mouse Es Cells and Oocytes. *Genesis* 31:6–10.

Schalkwyk L C, Jung M, Daser A, Weiher M, Walter J, Himmelbauer H & Lehrach H (1999) Panel of Microsatellite Markers for Whole-Genome Scans and Radiation Hybrid Mapping and a Mouse Family Tree. *Genome Res* 9:878–887.

Scheller A, Oehlke J, Wiesner B, Dathe M, Krause E, Beyermann M, Melzig M & Bienert M (1999) Structural Requirements for Cellular Uptake of Alpha-Helical Amphipathic Peptides. *J Pept Sci* 5:185–194.

Schena M, Shalon D, Heller R, Chai A, Brown P O & Davis R W (1996) Parallel Human Genome Analysis: Microarray-Based Expression Monitoring of 1000 Genes. *Proc Natl Acad Sci USA* 93:10614–10619.

Schlake T & Bode J (1994) Use of Mutated FLP Recognition Target (FRT) Sites for the Exchange of Expression Cassettes at Defined Chromosomal Loci. *Biochemistry* 33:12746–12751.

Schriml L M, Peterson R J, Gerrard B & Dean M (2000) Use of Denaturing HpIc to Map Human and Murine Genes and to Validate Single-Nucleotide Polymorphisms. *Biotechniques* 28:740–745.

Schuler G D, Boguski M S, Stewart E A et al. (1996) A Gene Map of the Human Genome. *Science* 274:540–546.

Schwarze S R, Ho A, Vocero-Akbani A & Dowdy S F (1999) In vivo Protein Transduction: Delivery of a Biologically Active Protein into the Mouse. *Science* 285:1569–1572.

Sclimenti C R, Thyagarajan B & Calos M P (2001) Directed Evolution of a Recombinase for Improved Genomic Integration at a Native Human Sequence. *Nucleic Acids Res* 29:5044–5051.

Sedivy J, Vogelstein B, Liber H, Hendrickson E & Rosmarin A (1999) Gene Targeting in Human Cells without Isogenic DNA. *Science* 283:9a.

Seibler J, Schubeler D, Fiering S, Groudine M & Bode J (1998) DNA Cassette Exchange in ES Cells Mediated by FLP Recombinase: An Efficient Strategy for Repeated Modification of Tagged Loci by Marker-Free Constructs. *Biochemistry* 37:6229–6234.

Shiga K, Fujita T, Hirose K, Sasae Y & Nagai T (1999) Production of Calves by Transfer of Nuclei from Cultured Somatic Cells Obtained from Japanese Black Bulls. *Theriogenology* 52:527–535.

Signer E N, Dubrova Y E, Jeffreys A J, Wilde C, Finch L M, Wells M & Peaker M (1998) DNA Fingerprinting Dolly. *Nature* 394:329–330.

Silhavy T J, Berman M L, Enquist L W & Cold Spring Harbor Laboratory. (1984) *Experiments with Gene Fusions.* Cold Spring Harbor Laboratory, Cold Spring Harbor, N.Y.

Slilaty S N & Aposhian H V (1983) Gene Transfer by Polyoma-Like Particles Assembled in a Cell-Free System. *Science* 220:725–727.

Snaith M R, Murray J A & Boulter C A (1995) Multiple Cloning Sites Carrying LoxP and FRT Recognition Sites for the Cre and FLP Site-Specific Recombinases. *Gene* 166:173–174.

Soriano P, Montgomery C, Geske R & Bradley A (1991) Targeted Disruption of the c-src Proto-Oncogene Leads to Osteopetrosis in Mice. *Cell* 64:693–702.

Stark W M, Boocock M R & Sherratt D J (1989) Site-Specific Recombination by Tn3 Resolvase. *Trends Genet* 5:304–309.

Stevens L (1983) Teratocarcinoma Stem Cells. In: *Cold Spring Harbor Conferences on Cell Proliferation; V.*10. Cold Spring Harbor Laboratory, Cold Spring Harbor, N.Y.

Strubing C, Ahnert-Hilger G, Shan J, Wiedenmann B, Hescheler J & Wobus A M (1995) Differentiation of Pluripotent Embryonic Stem Cells into the Neuronal Lineage in vitro Gives Rise to Mature Inhibitory and Excitatory Neurons. *Mech Dev* 53:275–287.

Tanaka A S, Tanaka M & Komuro K (1998) A Highly Efficient Method for the Site-Specific Integration of Transfected Plasmids into the Genome of Mammalian Cells Using Purified Retroviral Integrase. *Gene* 216: 67–76.

Tarantini F, LaVallee T, Jackson A, Gamble S, Carreira C M, Garfinkel S, Burgess W H & Maciag T (1998) The Extravesicular Domain of Synaptotagmin-1 Is Released with the Latent Fibroblast Growth Factor-1 Homodimer in Response to Heat Shock. *J Biol Chem* 273:22209–22216.

Taylor M, Vasil V & Vasil K (1993) Enhanced Gus Gene Expression in Cereal/Grass Cell Suspensions and Immature Embryos Using the Maize Ubiquitn-Based Plasmid PAHC25. *Plant Cell Reports* 12:491.

Thomas K R & Capecchi M R (1987) Site-Directed Mutagenesis by Gene Targeting in Mouse Embryo-Derived Stem Cells. *Cell* 51:503–512.

Thorpe H M & Smith M C (1998) In Vitro Site-Specific Integration of Bacteriophage DNA Catalyzed by a Recombinase of the Resolvase/Invertase Family. *Proc Natl Acad Sci USA* 95:5505–5510.

Thyagarajan B, Olivares E C, Hollis R P, Ginsburg D S & Calos M P (2001) Site-Specific Genomic Integration in Mammalian Cells Mediated by Phage phiC31 Integrase. *Mol Cell Biol* 21:3926–3934.

Tymms M J & Kola I (2001) *Gene Knockout Protocols.* Humana Press, Totowa, N.J., United States of America.

Umlauf S W & Cox M M (1988) The Functional Significance of DNA Sequence Structure in a Site-Specific Genetic Recombination Reaction. *EMBO J* 7:1845–1852.

U.S. Pat. No. 4,455,842
U.S. Pat. No. 4,940,935
U.S. Pat. No. 5,188,642
U.S. Pat. No. 5,445,934
U.S. Pat. No. 5,629,145
U.S. Pat. No. 5,707,798
U.S. Pat. No. 5,767,378
U.S. Pat. No. 5,780,296
U.S. Pat. No. 5,789,215
U.S. Pat. No. 5,792,904
U.S. Pat. No. 5,858,687
U.S. Pat. No. 5,859,307
U.S. Pat. No. 5,912,132
U.S. Pat. No. 5,965,352
U.S. Pat. No. 5,965,415
U.S. Pat. No. 5,986,082
U.S. Pat. No. 5,994,629
U.S. Pat. No. 6,001,654
U.S. Pat. No. 6,031,153
U.S. Pat. No. 6,033,906
U.S. Pat. No. 6,060,296
U.S. Pat. No. 6,069,010
U.S. Pat. No. 6,091,004
U.S. Pat. No. 6,093,531
U.S. Pat. No. 6,104,028
U.S. Pat. No. 6,107,623
U.S. Pat. No. 6,117,675
U.S. Pat. No. 6,129,911
U.S. Pat. No. 6,140,123
U.S. Pat. No. 6,174,690
U.S. Pat. No. 6,176,089
U.S. Pat. No. 6,190,910
U.S. Pat. No. 6,200,806
U.S. Pat. No. 6,221,647
U.S. Pat. No. 6,255,113
U.S. Pat. No. 6,284,541
U.S. Pat. No. 6,294,346
U.S. Pat. No. 6,319,692
U.S. Pat. No. 6,322,784
U.S. Pat. No. 6,333,192

Van Etten W J, Steen R G, Nguyen H, Castle A B, Slonim D K, Ge B, Nusbaum C, Schuler G D, Lander E S & Hudson T J (1999) Radiation Hybrid Map of the Mouse Genome. *Nat Genet* 22:384–387.

Venter J C, Adams M D, Myers E W et al. (2001) The Sequence of the Human Genome. *Science* 291:1304–1351.

Vieira J & Messing J (1982) The pUC Plasmids, an M13mp7-Derived System for Insertion Mutagenesis and Sequencing with Synthetic Universal Primers. *Gene* 19:259–268.

Wahler D & Reymond J L (2001) Novel Methods for Biocatalyst Screening. *Curr Opin Chem Biol* 5:152–158.

Wakayama T & Yanagimachi R (1999) Cloning of Male Mice from Adult Tail-Tip Cells. *Nat Genet* 22:127–128.

Wakayama T, Perry A C, Zuccotti M, Johnson K R & Yanagimachi R (1998) Full-Term Development of Mice from Enucleated Oocytes Injected with Cumulus Cell Nuclei. *Nature* 394:369–374.

Weitzer G, Milner D J, Kim J U, Bradley A & Capetanaki Y (1995) Cytoskeletal Control of Myogenesis: A Desmin Null Mutation Blocks the Myogenic Pathway During Embryonic Stem Cell Differentiation. *Dev Biol* 172:422–439.

Wells C & Brown S D (2000) Genomics Meets Genetics: Towards a Mutant Map of the Mouse. *Mamm Genome* 11:472–477.

Wells D N, Misica P M & Tervit H R (1999) Production of Cloned Calves Following Nuclear Transfer with Cultured Adult Mural Granulosa Cells. *Biol Reprod* 60:996–1005.

Wiles M V & Keller G (1991) Multiple Hematopoietic Lineages Develop from Embryonic Stem (ES) Cells in Culture. *Development* 111:259–267.

Wilmut I, Schnieke A E, McWhir J, Kind A J & Campbell K H (1997) Viable Offspring Derived from Fetal and Adult Mammalian Cells. *Nature* 385:810–813.

Wobus A, Rohwedel J & Strubing C (1997) In Vitro Differentiation of Embryonic Stem Cells. In: *Methods in Developmental Toxicology and Biology.* pp 1–17. Blackwell Science, Berlin/Vienna.

Wobus A, Guan K & Pich U (2001) In Vitro Differentiation of Embryonic Stem Cells and Analysis of Cellular Phenotypes. In: *Gene Knockout Protocols.* pp 263–286. Humana Press, Totowa, N.J., United States of America.

Wobus A M, Wallukat G & Hescheler J (1991) Pluripotent Mouse Embryonic Stem Cells Are Able to Differentiate into Cardiomyocytes Expressing Chronotropic Responses to Adrenergic and Cholinergic Agents and Ca2+ Channel Blockers. *Differentiation* 48:173–182.

Wolfgang W & Gossler A (2000) Gene Trap Strategies in ES Cells. In: *Gene Targeting : A Practical Approach,* 2nd ed. pp 207–254. Oxford University Press, Oxford.

Wu X & Maizels N (2001) Substrate-Specific Inhibition of RecQ Helicase. *Nucleic Acids Res* 29:1765–1771.

Xu T, Wang W, Zhang S, Stewart R A & Yu W (1995) Identifying Tumor Suppressors in Genetic Mosaics: The *Drosophila* Lats Gene Encodes a Putative Protein Kinase. *Development* 121:1053–1063.

Yaspo M L (2001) Taking a Functional Genomics Approach in Molecular Medicine. *Trends Mol Med* 7:494–501.

Zakhartchenko V, Alberio R, Stojkovic M et al. (1999) Adult Cloning in Cattle: Potential of Nuclei from a Permanent Cell Line and from Primary Cultures. *Mol Reprod Dev* 54:264–272.

Zamore P D (2001) RNA Interference: Listening to the Sound of Silence. *Nat Struct Biol* 8:746–750.

Zhang P, Li M Z & Elledge S J (2002) Towards Genetic Genome Projects: Genomic Library Screening and Gene-Targeting Vector Construction in a Single Step. *Nat Genet* 30:31–39.

It will be understood that various details of the presently claimed subject matter can be changed without departing from the scope of the presently claimed subject matter. Furthermore, the foregoing description is for the purpose of illustration only, and not for the purpose of limitation--the presently claimed subject matter being defined by the claims.

What is claimed is:

1. A method for preparing a homozygous cellular library comprising:
    (a) providing a heterozygous cellular library comprising a plurality of isolated parent cells, wherein:
        (i) the plurality of isolated parent cells comprise a plurality of different genetic modifications; and
        (ii) each of the plurality of isolated parent cells comprises a marked chromosome pair comprising a first selectable marker at a first position distal to a first site-specific recombination site on a first chromosome of the marked chromosome pair, and a second selectable marker at a second position distal to a second site-specific recombination site of a second homologous chromosome of the marked chromosome pair, wherein the first and second selectable markers are both selected from the group consisting of dominant, negative selectable markers and recessive, positive selectable markers, thereby permitting recovery of the marked chromosome pair; and
        (iii) the plurality of isolated parent cells comprises a randomly mutagenized population of isolated cells;
    (b) providing a site-specific recombinase to the plurality of isolated parent cells, thereby inducing site-specific mitotic recombination in the plurality of isolated parent cells;
    (c) culturing the plurality of parent cells, whereby a population of daughter cells is produced;
    (d) replica plating the population of daughter cells;
    (e) selecting one replica of the population of daughter cells for each of the first and the second selectable markers; and
    (f) isolating at least one daughter cell comprising a homozygosed first chromosome of the marked chromosome pair and at least one daughter cell comprising a homozygosed second homologous chromosome of the marked chromosome pair, whereby a homozygous cellular library is prepared.

2. The method of claim 1, wherein each cell of a randomly mutagenized population of isolated cells comprises one or more heterozygous genetic modifications.

3. The method of claim 2, wherein the one or more heterozygous genetic modifications comprise genetic modifications produced by a method selected from the group consisting of chemical mutagenesis, ultraviolet radiation, X-ray radiation, exposure to inhibitors of DNA repair, and combinations thereof.

4. The method of claim 1, wherein the plurality of isolated parent cells comprises cells selected from the group consisting of stem cells, precursor cells, and differentiated cells.

5. The method of claim 4, wherein the stem cells comprise embryonic stem cells.

6. The method of claim 1, wherein the plurality of isolated parent cells comprise animal cells.

7. The method of claim 6, wherein the animal cells comprise human cells.

8. The method of claim 1, wherein the plurality of isolated parent cells comprise plant cells.

9. The method of claim 1, wherein the first and second site-specific recombination sites each comprises a centromeric position.

10. The method of claim 1, wherein
    (a) the first selectable marker is a dominant, positive selectable marker;
    (b) the second selectable marker is a dominant, positive selectable marker; or
    (c) the first and second selectable markers are dominant, positive selective markers.

11. The method of claim 1, wherein the first and second site-specific recombination sites each comprises a lox site.

12. The method of claim 1, wherein the first and second site-specific recombination sites each comprises an FRT site.

13. The method of 1, wherein the first and second site-specific recombination sites each comprises an att site.

14. The method of 1, wherein the first and second site-specific recombination sites can recombine to produce a stable first recombination event.

15. The method of claim 14, wherein the first site-specific recombination site comprises a lox66 site, and wherein the second site-specific recombination site comprises a lox71 site.

16. The method of claim 14, wherein the first site-specific recombination site comprises an attB site, and wherein the second site-specific recombination site comprises an attP site.

17. The method of claim 1, wherein the inducing site-specific recombination comprises contacting the cells with a site-specific recombinase.

18. The method of claim 17, wherein the site-specific recombinase is selected from the group consisting of a Cre recombinase, a FLP recombinase, and an Int recombinase.

19. The method of claim 17, wherein the site-specific recombinase comprises a cell-permeable recombinase.

20. The method of claim 19, wherein the cell-permeable recombinase comprises a cell-permeable Cre recombinase.

21. The method of claim 1, wherein the culturing further comprises inducing the daughter cells to differentiate.

* * * * *